United States Patent [19]

Sestanj et al.

[11] Patent Number: 4,600,724

[45] Date of Patent: * Jul. 15, 1986

[54] N-NAPHTHOYLGLYCINE DERIVATIVES

[75] Inventors: Kazimir Sestanj, St. Laurent; Nedumparambil A. Abraham, Dollard des Ormeaux; Francesco Bellini, Mount Royal; Adi Treasurywala, Point Claire, all of Canada

[73] Assignee: Ayerst, McKenna & Harrison, Inc., Montreal, Canada

[*] Notice: The portion of the term of this patent subsequent to Jul. 5, 2000 has been disclaimed.

[21] Appl. No.: 756,139

[22] Filed: Jul. 17, 1985

Related U.S. Application Data

[62] Division of Ser. No. 530,457, Sep. 9, 1983, Pat. No. 4,568,693, which is a division of Ser. No. 321,306, Nov. 13, 1981, Pat. No. 4,439,617.

[30] Foreign Application Priority Data

Mar. 2, 1981 [CA] Canada ............................ 372119

[51] Int. Cl.$^4$ .................. C07C 153/05; A61K 31/195
[52] U.S. Cl. ..................................... 514/510; 560/10; 562/427
[58] Field of Search .................... 560/10; 562/427; 514/510

[56] References Cited

U.S. PATENT DOCUMENTS 3,821,383  6/1974  Sestanj et al. ................ 424/258
4,391,816  7/1983  Sestanj ........................ 424/274

OTHER PUBLICATIONS

D. Dvornik et al., Science, 182, 1146 (1973).
M. J. Peterson et al., Metabolism, 28 (Suppl. 1), 456(1979).
A. Lawson and C. E. Searle, J. Chem. Soc., 1556(1957).
V. I. Cohen et al., Eur. J. Med. Chem., 5, 480(1976); see also Chem Asbtr., 86, 189582f (1977).
J. Voss and W. Walter, Justus Leibigs Ann. Chem., 716, 209 (1968); see also Chem. Abstr., 70, 11306a (1969).
Chem. Abstr., 61, 4333f(1964) for E. Cioranescu et al., Rev. Chim. Acad. Rep. Populaire Roumaine, 7 (2), 755(1962).

Primary Examiner—Michael L. Shippen

[57] ABSTRACT

Herein disclosed are N-naphthoylglycine derivatives having aldose reductase inhibiting activity. The derivatives are useful for treating diabetic complications.

20 Claims, No Drawings

N-NAPHTHOYLGLYCINE DERIVATIVES

This is a division of application Ser. No. 530,457, filed Sept. 9, 1983, now U.S. Pat. No. 4,568,693 which in turn is a division of application Ser. No. 321,306, filed Nov. 13, 1981, now U.S. Pat. No. 4,439,617.

RELATED APPLICATIONS

Related hereto are U.S. patent application Ser. No. 321,304, now U.S. Pat. No. 4,391,816, U.S. patent application Ser. No. 321,303 and U.S. application Ser. No. 321,304, now U.S. Pat. No. 4,391,825, all filed on the same data as this application.

This application relates to N-naphthoylglycine derivatives, therapeutically acceptable salts thereof, a process for their preparation, and to methods of use and to pharmaceutical compositions thereof. The derivatives have pharmacologic properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita et al., Biochem. Biophys. Acta, 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182, 1146 (1973), and to be useful for the treatment of diabetic complications such as diabetic cataracts, neuropathy, nephropathy and retinopathy, see K. Sestanj, N. Simard-Duquesne and D. M. Dvornik, U.S. Pat. No. 3,821,383, June 28, 1974. Other compounds having a similar utility are the thioxo-1H-benz[de]-isoquinoline-2(3H)-acetic acid derivatives of K. Sestanj, U.S. application Ser. No. 92,397, filed Nov. 8, 1979 and 1H-benz-[de]isoquinoline-2(3H)-acetic acid derivatives of K. Sestanj, U.S. application Ser. No. 92,604, filed Nov. 8, 1979. (S)-6-Fluoro-2,3-dihydrospiro(4H-1-benzopyran-4,4'-imidazolidine)-2',5'-dione(sorbinil) is still another compound that has received attention because of its aldose reductase inhibiting properties (see. M. J. Peterson et al., Metabolism, 28 (Suppl. 1), 456 (1979). Accordingly, these compounds represent an important new approach for the treatment of diabetes mellitus.

The present application discloses novel N-naphthoylglycine derivatives, represented below by formula I, which are effective inhibitors of aldose reductase. These new derivatives are structurally quite different from the above noted aldose reductase inhibitors. Close prior art compounds, on a structural basis, appear to be a group of thioacylaminoacids, e.g. N-phenylthioxomethyl-N-methylglycine, prepared by A. Lawson and C. E. Searle, J. Chem. Soc., 1556 (1957) as part of chemical investigation of the chemical properties of such compounds. These last mentioned compounds were prepared by thiobenzoylation of various amino acids with (thiobenzoylthio)acetic acid. An important structural difference between these compounds and the present derivatives is the different type of aromatic group substituted on the thione portion of the thioamide. Thioacylamides also have been reported [see Chem. Abstr., 86, 189582f (1977) for V. I. Cohen et al., Eur. J. Med. Chem., 5, 480 (1976) and Chem. Abstr., 70, 11306a (1969) for von J. Voss and W. Walter, Justus Leibigs Ann. Chem., 716, 209 (1968)]. The structures of the thioacylamides of Cohen et al and Voss et al differ from the structure of the present derivatives by having at least a different type of N-substitution. Another close prior art compound, on a structural basis, is N-[(1-naphthalenyl)carbonyl]glycine, [see Chem. Abstr., 61, 4333f (1964) for E. Cioranescu et al., Rev. Chim. Acad. Rep. Populaire Roumaine, 7 (2), 755 (1962)]. The compound, which has been used as a chemical intermediate, is distinguished from the compounds of the present invention by being an amide and not a thioamide.

SUMMARY OF THE INVENTION

The N-naphthoylglycine derivatives of this invention are represented by formula I

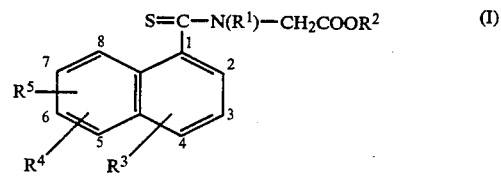

wherein $R^1$ is hydrogen, lower alkyl, lower alkenyl or phenylmethyl; $R^2$ is hydrogen or lower alkyl; $R^3$ is hydrogen, a lower alkoxy at a position 6 of the naphthalene ring, or a substituent at position 4, 5 or 8 of the naphthalene ring, the substituent being selected from the group consisting of lower alkyl, lower alkoxy, halo, cyano, nitro and trihalomethyl, and $R^4$ and $R^5$ each is hydrogen; or $R^3$ and $R^4$ each is a substituent at different positions selected from positions 3 to 7 of the naphthalene ring, the substituents being selected from the group consisting of lower alkyl, lower alkoxy, halo, trihalomethyl, (lower)alkoxy(lower)alkoxy, phenylmethoxy and phenylmethoxy substituted on the phenyl portion with a lower alkyl, lower alkoxy, halo or trihalomethyl, and $R^5$ is hydrogen; or $R^3$, $R^4$ and $R^5$ each is a substituent at different positions selected from positions 4, 5 and 6 of the naphthalene ring, the substituent being selected from the group consisting of lower alkoxy, halo and trihalomethyl; or a therapeutically acceptable salt with an organic or inorganic base of the compound of formula I wherein $R^2$ is hydrogen.

A group of preferred derivatives is represented by the compounds of formula I wherein $R^1$ is hydrogen, lower alkyl, 2-propenyl or phenylmethyl; $R^2$ is hydrogen or lower alkyl; $R^3$ is hydrogen, a lower alkoxy at position 6 of the naphthalene ring, or a substituent at positions 4, 5 or 3 of the naphthalene ring, the substituents being selected from the group consisting of lower alkyl, lower alkoxy, halo, cyano, nitro and trifluoromethyl, and $R^4$ and $R^5$ each is hydrogen; or $R^3$ and $R^4$ are a pair of substituents on the naphthalene ring, each substituent being at a different position of the ring, the pair of substituents being selected from the group of pairs consisting of 3-halo-4-lower alkoxy, 4,6-di(lower alkoxy), 5-halo-6-lower alkyl, 5-halo-6-lower alkoxy, 5,7-dihalo, 5-(trifluoromethyl)-6-lower alkoxy, 5-halo-6-(lower)alkoxy(lower)alkoxy, 5-halo-6-[3-(trifluoromethyl)-phenylmethoxy] and 5-halo-6-(4-chlorophenylmethoxy), and $R^5$ is hydrogen; or $R^3$, $R^4$ and $R^5$ each is a substituent on the naphthalene ring, each of the three substituents being at different positions on the ring, the three substituents being selected from the group of 4-lower alkoxy-5-halo-6-lower alkoxy and 4,6-di(lower alkoxy)-5-(trifluoromethyl); or a therapeutically acceptable salt with an organic or inorganic base of the compound of formula I wherein $R^2$ is hydrogen.

Another preferred group of the compounds is represented by the compounds of formula I wherein $R^1$ is hydrogen, lower alkyl or phenylmethyl; $R^2$ is hydrogen or lower alkyl; $R^3$ is 4-halo or 5-halo, and $R^4$ and $R^5$ each is hydrogen; or $R^3$ and $R^4$ are a pair of substituents on the naphthalene ring selected from the group of pairs consisting of 3-halo-4-lower alkoxy, 4,6-di(lower alkoxy), 5-halo-6-lower alkyl, 5-halo-6-lower alkoxy, 5,7-dihalo and 5-(trifluoromethyl)-6-lower alkoxy, and $R^5$ is hydrogen; or $R^3$ is 4-lower alkoxy, $R^4$ is 5-(trifluoromethyl) and $R^5$ is 6-lower alkoxy; or a therapeutically acceptable salt with an organic or inorganic base of the compound of formula I wherein $R^2$ is hydrogen.

A most preferred group of the compounds is represented by the compounds of formula I wherein $R^1$ is lower alkyl; $R^2$ is hydrogen; $R^3$ is 5-halo and $R^4$ and $R^5$ each is hydrogen; or $R^3$ and $R^4$ are a pair of substituents on the naphthalene ring selected from the group of pairs consisting of 3-halo-4-lower alkoxy, 5-halo-6-lower alkoxy and 5-(trifluoromethyl)-6-lower alkoxy, and $R^5$ is hydrogen; or $R^3$ is 4-lower alkoxy, $R^4$ is 5-(trifluoromethyl) and $R^5$ is 6-lower alkoxy; or a therapeutically acceptable salt thereof with an organic or inorganic base.

The compounds of formula I can be prepared by a process described hereinafter.

A method is provided for preventing or relieving diabetes mellitus associated complications in a diabetic mammal by administering to said mammal a prophylactic or alleviating amount of the compound of formula I or therapeutically acceptable salt thereof with an organic or inorganic base.

The compound of formula I, or a therapeutically acceptable salt thereof with an organic or inorganic base, when admixed with a pharmaceutically acceptable carrier, forms a pharmaceutical composition which can be used according to the preceding method.

DETAILED DESCRIPTION OF THE INVENTION

The compounds of this invention, represented by formula I, can exist in rotameric forms. More explictly, mesomerism imparts a partial double bond character to the carbon-nitrogen bond of the thioamide group. This partial double bond character leads to restricted rotation about the carbon nitrogen bond giving rise to cis and trans rotamers, the restricted rotation being augmented by the bulkiness of neighboring groups. Interconversion of the rotamers is possible and is dependent on the physical environment. As evidenced by its physical properties, the thermodynamically more stable rotamer exists exclusively in the crystalline state of the compound and is the predominant isomer present in equilabrated solutions. Furthermore, the more stable rotamer is the more pharmacologically active. The less stable rotamer can be separated from the more stable rotamer by high performance liquid chromatography or by thin layer chromatography. The rotameric forms are included within the scope of this invention. For brevity, the compounds of this invention, including their rotameric forms, are referred to herein as compounds of formula I.

The term "lower alkyl" as used herein means a straight chain alkyl radical containing from one to four carbon atoms or a branched chain alkyl radical containing three or four carbon atoms and includes methyl, ethyl, propyl, 1-methylethyl, butyl, 2-methylpropyl and 1,1-dimethylethyl. Preferred lower alkyl radicals contain from one to three carbon atoms.

The term "lower alkenyl" as used herein means a straight chain alkenyl radical containing from two to six carbon atoms, or a branched chain alkenyl radical containing from four to six carbon atoms and includes, for example, ethenyl, 2-propenyl, 2-methyl-2-propenyl and 2-ethyl-3-butenyl. Preferred lower alkenyl radicals contain two to three carbon atoms.

The term "lower alkoxy" as used herein means a straight chain alkoxy radical containing from one to six carbon atoms, preferably one to three carbon atoms, or a branched chain alkoxy radical containing three or four carbon atoms, and includes methoxy, ethoxy, 1-methylethoxy, butoxy and hexanoxy.

The term "halo" as used herein means a halo radical and includes fluoro, chloro, bromo and iodo.

The term "ar" as used mean an aromatic radical containing at least one benzene ring. The preferred aromatic radical is phenyl.

The compounds of formula I wherein $R^2$ is hydrogen form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of this invention and their addition salts with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the present therapeutic agents will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration a 0.05–0.2% solution may be administered dropwise to the eye. The frequency of instillation varies with the subject under treatment from a drop every two or three days to once daily. For oral or parenteral administration a preferred level of dosage ranges from about 0.1 mg to about 200 mg per kilo of body weight per day, although aforementioned variations will occur. However, a dosage level that is in the range of from about 0.5 mg to about 30 mg per kilo of body weight per day is most satisfactory.

Unit dosage forms such as capsules, tablets, pills and the like may contain from about 5.0 mg to about 250 mg of the active ingredients of this invention, preferably with a significant quantity of a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents for example, magnesium stearate.

Syrups or elixirs suitable for oral administration can be prepared from water soluble salts, for example, sodium N-[[5-(trifluoromethyl)-6-methoxy-1-naphthalenyl]thioxomethyl]-N-methylglycinate, and may advantageously contain glycerol and ethyl alcohol as solvents or preservatives.

The compound of formula I, or a therapeutically acceptable salt thereof, also can be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compound of formula I, or a therapeutically acceptable salt thereof, can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 34 ed., Medical Economics Co., Oradell, N.J., U.S.A., 1980. When used in combination, the compound of formula I, or its therapeutically acceptable salt, is administered as described previously. The compound of formula I, or its therapeutically acceptable salt, can be administered with the oral hypoglycemic agent in the form of a pharmaceutical composition comprising effective amounts of each agent.

The aldose reductase inhibiting effects of the compounds of formula I and their pharmaceutically acceptable salts with organic or inorganic bases can be demonstrated by employing an in vitro testing procedure similar to that described by S. Hayman and J. H. Kinoshita, J. Biol. Chem., 240, 877 (1965). In the present case the procedure of Hayman and Kinoshita is modified in that the final chromatography step is omitted in the preparation of the enzyme from bovine lens.

The following results were obtained when the foregoing listed compounds of formula I were evaluated in the above in vitro test.

third group was fed a diet prepared by mixing a given amount of the test compound with the galactose containing diet. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues were frozen and can be kept up to two weeks before being analyzed for dulcitol.

(c) The polyol determination was performed by a modification of the procedure of M. Kraml and L. Cosyns, Clin. Biochem., 2, 373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of

| Compound of Formula I($R^5$ = H) | | | | Example In Which Compound Is Prepared | % Inhibition at Different Mola Concentration (in vitro) | | |
|---|---|---|---|---|---|---|---|
| $R^1$ | $R^2$ | $R^3$ | $R^4$ | | $10^{-5}$ | $10^{-6}$ | $10^{-7}$ |
| $CH_3$ | $CH_3$ | 5-Br | H | 3 | 8 | | |
| $CH_3$ | $CH_3$ | 5-$CF_3$ | 6-$CH_3O$ | 23 | 9 | | |
| $CH_3$ | H | 5-Br | H | 32 | 93 | 87 | 47 |
| H | H | 3-Cl | 4-$CH_3O$ | 32 | 61 | 16 | |
| $CH_3$ | H | 4-Br | H | 33 | 91 | 77 | 32 |
| $CH_3$ | H | 8-Br | H | 34 | 88 | 75 | 24 |
| $CH_3$ | H | 5-$CH_3O$ | H | 35 | 83 | 64 | 17 |
| $CH_3$ | H | 5-$CH_3$ | H | 36 | 89 | 74 | 26 |
| $CH_3$ | H | 5-Br | 6-$CH_3(CH_2)_4O$ | 37 | 93 | 91 | 55 |
| $CH_3$ | H | 5-CN | H | 38 | 89 | 79 | 32 |
| $CH_3$ | H | 5-$NO_2$ | H | 39 | 91 | 83 | 43 |
| $CH_3$ | H | 5-Cl | H | 40 | 91 | 83 | 40 |
| $CH_3$ | H | 5-Br | 6-$CH_3O$ | 41 | 99 | 91 | 72 |
| $CH_3$ | H | 5-Br | 6-$CH_3$ | 42 | 92 | 88 | 55 |
| $CH_3$ | H | H | H | 43 | 85 | 51 | 13 |
| $CH_3$ | H | 4-Cl | H | 44 | 88 | 73 | 25 |
| $CH_3$ | H | 3-Cl | 4-$CH_3O$ | 45 | 85 | 78 | 33 |
| $CH_3$ | H | 5-Cl | 7-Cl | 46 | 88 | 75 | 29 |
| $CH_3$ | H | 5-I | 6-$CH_3O$ | 47 | 98 | 95 | 72 |
| $CH_3$ | H | 5-CN | 6-$CH_3O$ | 48 | 98 | 93 | 74 |
| $CH_3$ | H | 5-Br | 6-$CH_3O(CH_2)_3O$ | 49 | 92 | 87 | 38 |
| $CH_3$ | H | 5-$CH_2$=C($CH_3$) | H | 50 | 92 | 74 | 19 |
| $CH_3$ | H | 5-$(CH_3)_2CH$ | H | 51 | 91 | 72 | 21 |
| $CH_3$ | H | 5-$CF_3$ | 6-$CH_3O$ | 52 | 98 | 94 | 65 |
| $CH_3$ | H | 5-Br | 6-[(3-$CF_3$—$C_6H_4$)$CH_2O$] | 53 | 86 | 37 | 11 |
| $CH_3$ | H | 5-Br | 6-[(4-Cl—$C_6H_4$)$CH_2O$] | 53a | 88 | 44 | 4 |
| $CH_3$ | H | 5-$CF_3$ | H | 53b | 93 | 84 | 33 |
| H | H | 5-Br | H | 54 | 54 | 14 | |
| n-$C_3H_7$ | H | 5-Br | H | 55 | 91 | 70 | 19 |
| $CH_2$=CH—$CH_2$ | H | 5-Br | H | 56 | 92 | 77 | 27 |
| $C_2H_5$ | H | 5-Br | H | 57 | 85 | 72 | 24 |
| n-$C_4H_9$ | H | 5-Br | H | 58 | 86 | 65 | 19 |
| $CH_2C_6H_5$ | H | 5-Br | H | 59 | 86 | 69 | 20 |

The aldose reductase inhibiting property of the compounds of this invention and the utilization of the compounds in preventing, diminishing and alleviating diabetic complications are demonstrable in experiments using galactosemic rats, see Dvornik et al., cited above. Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent laboratory chow, Purina) and glucose at 20% (w/w %) concentration. The untreated galactosemic group was fed a similar diet in which galactose is substituted for glucose. The an aqueous trichloroacetic acid solution. (N.B.: For each experiment the average value found in the tissue from rats fed the glucose diet was subtracted from the individual values found in the corresponding rat tissue to obtain the amount of polyol accumulated.)

The following tabulated results show that the compounds of this invention diminish the accumulation of dulcitol in the lenses and sciatic nerves of rats fed galactose. The figures under L and N represent the percentage decrease of dulcitol accumulation in the tissues of the lens and sciatic nerve, respectively, for treated rats as compared to untreated rats.

| Compound of Formula I | | | | | Dose | | |
|---|---|---|---|---|---|---|---|
| $R^1$ | $R^2$ | $R^3$ | $R^4$ | $R^5$ | mg/kg/day | L | N |
| $CH_3$ | H | 5-Br | H | H | 189 | 24 | 79 |
|  |  |  |  |  | 121 | 20 | 70 |
|  |  |  |  |  | 62 | 14 | 53 |
| $CH_3$ | H | 5-Cl | H | H | 156 | 34 | 70 |
| $CH_3$ | H | 5-Br | 6-$CH_3O$ | H | 162 | 34 | — |
|  |  |  |  |  | 58 | — | 78 |
|  |  |  |  |  | 29 | — | 58 |
|  |  |  |  |  | 15 | — | 32 |
| $CH_3$ | H | 3-Cl | 4-$CH_3O$ | H | 163 | 15 | — |
|  |  |  |  |  | 25 | — | 27 |
| $CH_3$ | H | 5-Cl | 7-Cl | H | 52 | 29 | 45 |
| $CH_3$ | H | 5-$CF_3$ | 6-$CH_3O$ | H | 26 | 15 | 94 |
| $CH_3$ | $CH_3$ | 5-$CF_3$ | 6-$CH_3O$ | H | 11 | 10 | 44 |
| $CH_3$ | H | 5-$CF_3$ | H | H | 11 | 2 | 36 |
| $CH_3$ | H | 6-$CH_3O$ | H | H | 162 | — | 32 |
| $CH_3$ | H | 4-$CH_3O$ | 5-$CF_3$ | 6-$CH_3O$ | 144 | 33 | 85 |
|  |  |  |  |  | 25 | — | 48 |

Process

The preparation of the compounds of formula I is illustrated by the following scheme wherein $R^1$, $R^3$, $R^4$ and $R^5$ are as defined hereinbefore and COOR is an ester group which may be, for example, a lower alkyl or an ar(lower)alkyl ester; i.e., R is lower alkyl or ar(lower)alkyl.

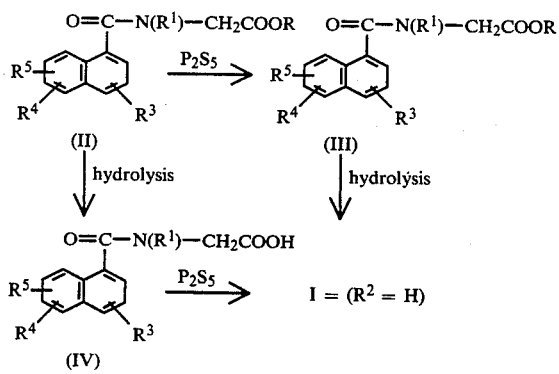

More specifically, a process for preparing the compounds of formula I comprises:

(a) reacting an amidoester of formula II wherein $R^1$, $R^3$, $R^4$ and $R^5$ are as defined herein and R is lower alkyl or ar(lower)alkyl with phosphorus pentasulfide to give the corresponding thioxoester of formula III wherein $R^1$, $R^3$, $R^4$, $R^5$ and R are as defined herein; or (b) hydrolyzing the thioxoester of formula III wherein $R^1$, $R^3$, $R^4$, $R^5$ and R are as defined herein to obtain the corresponding compound of formula I wherein $R^1$, $R^3$, $R^4$ and $R^5$ are as defined herein and $R^2$ is hydrogen; or (c) hydrolyzing the amidoester of formula II wherein $R^1$, $R^3$, $R^4$, $R^5$ and R are as defined herein to obtain the corresponding amidoacid of formula IV wherein $R^1$, $R^3$, $R^4$ and $R^5$ are as defined herein, and reacting the last-named compound with phosphorus pentasulfide to obtain the corresponding compound of formula I wherein $R^1$, $R^3$, $R^4$ and $R^5$ are as defined herein and $R^2$ is hydrogen.

Referring to the above section (a) of the last paragraph, the thioxoester of formula III includes those corresponding compounds of formula I wherein $R^2$ is lower alkyl, when R of the compound of formula III is lower alkyl. For clarity and convenience in the following discussion of the process, these latter compounds of formula I are included in the discussion and preparation of the compounds of formula III.

Still more specifically, the starting material of formula II can be prepared by coupling a naphthalenecarboxylic acid of formula V wherein $R^3$, $R^4$ and $R^5$ are as defined herein with an aminoacid ester of formula VI wherein $R^1$ and R are as defined herein.

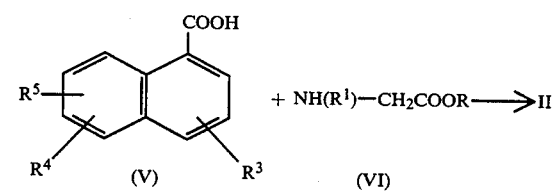

The compounds of formula V and VI are known or can be prepared by known methods. For example, see "Elsevier's Encyclopaedia of Organic Chemistry," F. Radt, Ed., Series III, Vol. 12B, Elsevier Publishing Co., Amsterdam, 1953, pp 3965–4473. The preparation of a number of the naphthalenecarboxylic acids is illustrated by examples 1 and 1a to 1j described hereinafter. The coupling of the naphthalenecarboxylic acid V and the amino acid ester VI is done preferably by the "carboxyl activation" coupling procedure. Descriptions of carboxyl-activating groups are found in general textbooks of peptide chemistry; for example K. D. Kopple, "Peptides and Amino Acids," W. A. Benjamin, Inc., New York, 1966, pp. 45–51, and E. Schröder and K. Lübke, "The Peptides;" Vol. 1, Academic Press, New York, 1965, pp. 77–128. Examples of the activated form of the terminal carboxyl are the acid chloride, acid bromide, anhydride, azide, activated ester, or O-acyl urea obtained from a dialkylcarbodiimide. Preferred activated forms of the carboxyl are the acid chloride or the 1-benzotriazolyl, 2,4,5-trichlorophenyl or succinimido activated esters.

Returning to the flow diagram again, the amidoester of formula II is reacted under anhydrous conditions with about two to five molar equivalents of phosphorus pentasulfide in an inert solvent, e.g. xylene or toluene, to obtain the corresponding thioxoester of formula III. This reaction is performed conveniently at temperatures ranging from 80° to about 150° C. and at times ranging from 20 minutes to four hours. Preferably, the reaction is performed in the presence of an organic base for instance, N-ethyl morpholine, triethylamine or pyridine.

Thereafter, the thioxoester of formula III is hydrolyzed with a hydrolyzing agent to give the corresponding product of formula I in which $R^2$ is hydrogen. Generally speaking, this conversion is most conveniently performed by employing a base as the hydrolyzing agent. The hydrolysis is performed in the presence of sufficient water, followed by acidification of the reaction mixture, to yield the desired acid. However, it should be understood that the manner of hydrolysis for the process of this invention is not intended to be limited to basic hydrolysis since hydrolysis under acidic conditions and other variations, for example, treatment with lithium iodide in collidine (see. L. F. Fieser and M. Fieser, "Reagents for Organic Synthesis", John Wiley and Sons, Inc., New York, 1969, pp. 615–617), also are applicable. Hydrolysis under acidic conditions is preferred when the ester is a tert butyl ester.

For basic hydrolysis, a preferred embodiment involves subjecting the ester to the action of a strong base, for example, sodium or potassium hydroxide, in the presence of sufficient water to effect hydrolysis of the ester. The hydrolysis is performed using a suitable solvent, for example, methanol, ethanol or 2-methoxyethanol. The reaction mixture is maintained at a temperature of from about 25° to 100° C. or at the reflux temperature of the solvent employed until hydrolysis occurs. Usually from 10 minutes to 6 hours is sufficient for this hydrolysis. The reaction mixture is then rendered acidic with an acid, for example, acetic acid, hydrochloric acid or sulfuric acid to release the free acid.

Alternatively, the amidoester of formula II can be hydrolyzed under the same conditions as described hereinbefore to give the corresponding amidoacid of formula IV wherein $R^1$, $R^3$, $R^4$ and $R^5$ are as defined herein. The latter compound, when reacted with phosphorus pentasulfide in the manner described hereinbefore, then gives the corresponding compound of formula I wherein $R^1$, $R^3$, $R^4$ and $R^5$ are as defined herein and $R^2$ is hydrogen. Note that the standard first step of the work up of the pentasulfide reaction mixture requires that the reaction mixture be decomposed in water. This action causes any corresponding thioacid, present in the reaction mixture as a result of the carboxy group reacting with phosphorus pentasulfide, to be converted to the desired carboxylic acid.

The aminoacid of formula IV also can be prepared by a previously reported process involving the reaction of the appropriate naphthalenecarboxylic acid chloride with the appropriate aminoacid corresponding to the aminoacid ester of formula VI in the presence of a base (proton acceptor). This process has been used to prepare N-[(1-naphthalenyl)carbonyl]glycine, see Chem. Abstr., 61, 4333 f (1964) for E. Cioranescu, et al., Rev. Chim., Acad. Rep. Populaire Roumaine, 7 (2), 755 (1962). However, this known process for preparing N-[(1-naphthalenyl)carbonyl]glycine is inferior, based on yields, to the present process.

An interesting aspect of this invention is that certain amidoesters of formula II and certain amidoacids of formula IV having the following formula

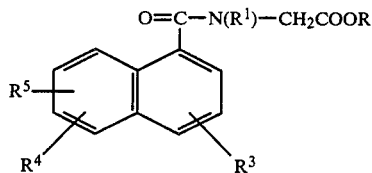

wherein $R^1$ is lower alkyl, lower alkenyl or phenylmethyl; $R^3$ is a substituent at position 4, 5 or 8 of the naphthalene ring, the substituent being selected from the group consisting of lower alkyl, lower alkoxy, halo, cyano, nitro and trihalomethyl, and $R^4$ and $R^5$ each is hydrogen; or $R^3$ and $R^4$ each is a substituent at different positions of the naphthalene ring, the positions selected from positions 3 to 7 and the substituents being selected from the group consisting of lower alkyl, lower alkoxy, halo, trihalomethyl, (lower)alkoxy(lower)alkoxy, phenylmethoxy and phenylmethoxy substituted on the phenyl portion with a lower alkyl, lower alkoxy, halo or trihalomethyl and $R^5$ is hydrogen; or $R^3$, $R^4$ and $R^5$ each is a substituent at different positions selected from positions 4,5 and 6 of the naphthalene ring, the substituent being selected from the group consisting of lower alkoxy, halo and trihalomethyl; and R is hydrogen or lower alkyl; or a therapeutically acceptable salt thereof with an organic or inorganic base, also have aldose reductase inhibiting effects. For example, in the above noted in vitro test, the following results were obtained for the amidoacids, described in example 60: N-[(5-bromo-1-naphthalenyl)carbonyl]-N-methylglycine ($10^{-5}$, 64%; $10^{-6}$, 21%); and N-[[5-(trifluoromethyl)-6-methoxy-1-naphthalenyl]carbonyl]-N-methylglycine ($10^{-5}$, 94%; $10^{-6}$, 93%; $10^{-7}$, 60%). Accordingly, the latter amidoesters, amidoacids and the therapeutically acceptable salts with organic or inorganic bases, of the amidoacids are included within the scope of this invention.

The following examples illustrate further this invention.

EXAMPLE 1

5-(1-Methylethenyl)-1-naphthalenecarboxylic Acid (V, $R^3=5—CH_2=C(CH_3)$ and $R^4$ and $R^5=H$).

In a nitrogen atmosphere, a solution of 1-bromo-5-(1-methylethenyl)-naphthalene [14.21 g, described by W. F. Short and H. Wang, J. Chem. Soc., 991 (1950)] in diethyl ether (140 ml) was added dropwise to a mixture of ethyl magnesium bromide (prepared from 2.94 g of magnesium and 4.29 ml of ethyl bromide) in diethyl ether (30 ml) at 0° C. The mixture was stirred at 20° C. for 18 hr and then heated at reflux for 1 hr. The cooled solution was poured onto an excess of solid carbon dioxide. The mixture was dissolved in diethyl ether. The resulting solution was washed with a 2N aqueous solution of $H_2SO_4$, brine and 10% aqueous NaHCO$_3$(4x). The basic washes were combined and made acidic (pH 3) with 6N aqueous HCl. The resulting solid was collected, washed with water and dried to give 9.7 g of the title compound; mp 138°-140° C.; NMR(CDCl$_3$) δ 2.15 (s, 3H), 5.0 & 5.38 (2s, 2H), 8.0 (m, 6H), 10.75 (s, 1H).

EXAMPLE 1a 5-(1-Methylethyl)-1-naphthalenecarboxylic Acid (V, $R^3=5—(CH_3)_2CH$ and $R^4$ and $R^5=H$)

5-(1-Methylethenyl)-1-naphthalenecarboxylic acid (4.36 g, described in Example 1), dissolved in ethanol (150 ml), was hydrogenated using 5% palladium on charcoal as catalyst at 20° C. Absorption of hydrogen was complete after 3 hr. The catalyst was removed by filtration. The filtrate was evaporated to give the title compound; mp 148°-150° C.; NMR(CDCl$_3$) δ 1.4 (d, J=7 Hz, 6H), 3.75 (septuplet, J=7 Hz, 1H), 8.0 (m, 6H), 10.1 (s, 1H).

EXAMPLE 1b

5-Bromo-6-methoxy-1-naphthalenecarboxylic Acid (V, $R^3=5—Br$, $R^4=6—CH_3O$ and $R^5=H$)

A solution of bromine (2.49 ml, 45 mmoles) in glacial acetic acid (50 ml) was added dropwise to a stirred solution of 6-methoxy-1-naphthalenecarboxylic acid [b 8.9 g, 44 mmoles, described by C. C. Price, et al., J. Am. Chem. Soc., 69, 2261 (1947)] in glacial acetic acid (300 ml), cooled in an ice bath. The resulting precipitate was collected and washed with acetic acid and then water. Crystallization of collected precipitate from glacial acetic acid gave the title compound; mp 262°-264° C.;

NMR(DMSO-d$_6$) δ 3.96 (s, 3H), 7.5–7.8 (m, 3H), 7.95 (d, 1H), 8.25 (d, 1H), 8.82 (d, 1H).

EXAMPLE 1c

5-Bromo-6-methyl-1-naphthalenecarboxylic Acid (V, R$^3$=5—Br, R$^4$=6—CH$_3$ and R$^5$=H)

By following the procedure of Example 1b, but replacing 6-methoxy-1-naphthalenecarboxylic acid with an equivalent amount of 6-methyl-1-naphthalenecarboxylic acid, described by C. C. Price et al., J. Am. Chem. Soc., 63, 1857 (1941), the title compound; mp 253°–255° C. [after crystallization from ethanol-methanol (3:1)], NMR (DMSO-d$_6$) δ 2.6 (s, 3H), 8.0 (m, 5H), 10.5 (broad, 1H), was obtained.

EXAMPLE 1d

3-Chloro-4-methoxy-1-naphthalenecarboxylic Acid (V, R$^3$=3—Cl, R$^4$=4—CH$_3$O and R$^5$=H)

3-Chloro-4-methoxy-1-naphthalenecarboxaldehyde [15.5 g, 70.2 mmoles, described by A. J. Ablewhite and K. R. H. Wooldridge, J. Chem. Soc. (C), 2488 (1967)] was added to a suspension of silver oxide in 10% sodium hydroxide (16.9 g of sodium hydroxide in 170 ml of water) and dioxane (100 ml). The mixture was stirred and heated at 80° C. for 7 hr. The precipitate was removed by filtration through diatomaceous earth (sold under the trademark Celite). The clear filtrate was evaporated to dryness. The residue was dissolved in water. The solution was acidified and the resulting precipitate was separated by filtration. The precipitate was dissolved in ethyl acetate. The resulting solution was extracted with saturated sodium bicarbonate solution. The combined aqueous extracts were acidified. The resulting precipitate was separated by filtration and recrystallized from ethanol-water to give the title compound; mp 187°–189° C.; NMR (DMSO-d$_6$) δ 4.0 (s, 3H), 8.15 (m, 5H), 13.3 (broad 1H); IR (Nujol*) 2900, 1700, 1260, 1160 cm$^{-1}$; UVλmax (EtOH) 303 (ε7,400), 231 (56,300); Anal. Calcd: C, 60.90% H, 3.83% Found: C, 60.71% H, 3.87%.

*Nujol is a trademark for a brand of white mineral oil*

EXAMPLE 1e 5,7-Dichloro-1-naphthalenecarboxylic Acid (V, R$^3$=5—Cl, R$^4$=7—Cl and R$^5$=H)

Sulfuryl chloride (36.8 g, 273 mmoles) was added dropwise to a stirred suspension of benz[c,d]indole-2(1H)-one (20 g, 119 mmoles) in glacial acetic acid (275 ml) at 20° to 22° C. The mixture was heated at reflux for 1.5 hr, cooled and filtered. The collected solid was washed with glacial acetic acid and recrystallized from toluene to afford 6,8-dichloro-benz[c,d]indole-2(1H)-one, mp 265° C., described by Y. T. Rozhinskii, Zhur. Org. Khim., 8, 2388 (1972). A mixture of the latter compound (14 g, 58.8 mmoles) in 2% aqueous sodium hydroxide was refluxed for 4 hr. The mixture was cooled, mixed with sodium nitrite (3.8 g, 55 mmoles) and added dropwise to a cooled (0°–5° C.) solution of concentrated sulfuric acid (45 ml) in water (180 ml). The diazonium salt was salted out by addition of sodium bromide, collected by filtration and while still wet (drying dangerous) was added to a solution of sodium hypophosphate (39.2 g of NaH$_2$PO$_2$.H$_2$O) in water (100 ml). The mixture was stirred at 20°–22° C. for 48 hr. The resulting solid was collected by filtration and suspended in saturated sodium bicarbonate (300 ml). The insoluble material was collected by filtration and resuspended in hot, saturated sodium bicarbonate (200 ml). The suspension was filtered and the filtrate was cooled. The resulting precipitate of the sodium salt of the product was collected by filtration. The free acid was prepared by suspending the sodium salt in water and rendering the suspension acidic. More product was obtained by acidification of filtrates of the sodium salt. The combined crops were recrystallized from ethanol to yield 5.8 g of the title compound; mp 253°–254° C.; NMR (DMSO-d$_6$) δ 8.3 (m, 5H), 10.6 (broad, 1H), UVλmax (EtOH) 333 nm (ε 2,350), 298 (7,000), 230 (53,300).

EXAMPLE 1f

5-Iodo-6-methoxy-1-naphthalenecarboxylic Acid (V, R$^3$=5—I, R$^4$=6—CH$_3$O and R$^5$=H)

Iodine (7.08 g) and iodic acid (2.78 g) were added to a stirred solution of 6-methoxy-1-naphthalenecarboxylic acid methyl ester [15 g, 69.4 mmoles, described by C. C. Price et al., J. Amer. Chem. Soc., 69, 2261 (1947)] in 80% acetic acid (110 ml) and 98% sulfuric acid (0.97 ml). The solution was heated at 50° C. for 5 hr, cooled and poured into water (100 ml). After the addition of sodium bisulfite to destroy the unreacted iodine, the precipitate was collected, washed with water and recrystallized from ethanol to afford the corresponding methyl ester of the title compound; mp 98°–99° C.; NMR (CDCl$_3$) δ 3.95 (s, 3H), 4.00 (s, 3H), 8.00 (m, 5H). A mixture of the latter ester (7.1 g, 21 mmoles), 10% aqueous sodium hydroxide (35 ml) and methanol (19.5 ml) was heated at reflux for 1 hr. The solution was cooled to ice bath temperature and made acidic with 1N aqueous hydrochloride. The resulting precipitate was collected, washed with water and dried under reduced pressure over phosphorus pentoxide to give 7 g of the title compound; mp 259°–261° C.; NMR (DMSO-d$_6$) δ 4.0 (s, 3H), 8.15 (m, 5H), 10.56 (broad, 1H).

EXAMPLE 1g

5-Cyano-6-methoxy-1-naphthalenecarboxylic Acid (V, R$^3$=5—CN, R$^4$=6—CH$_3$O and R$^5$=H)

A solution of bromine (26.6 g, 0.167 mole) in glacial acetic acid (25 ml) was added dropwise to a cooled suspension of 6-methoxy-1-naphthalenecarboxylic acid methyl ester (30 g, 0.13 9 moles) in glacial acetic acid (2.75 ml). The precipitate was collected, washed with water and crystallized from ethanol to give 33.3 g of 5-bromo-6-methoxy-1-naphthalenecarboxylic acid methyl ester; mp 119° C.; NMR (CDCl$_3$) δ 3.97 (s, 3H), 4.03 (s, 3H), 7.35 (d, J=9.25 Hz, 1H), 7.4 (m, 1H), 8.05 (d, J=6.75 Hz, 1H) 8.45 (d, J=8.25 Hz, 1H), 8.9 (d, J=9.25, 1H). The latter ester (10.1 g, 34 mmoles) and Cu$_2$(CN)$_2$.H$_2$O (3.4 g, 17 mmoles) in distilled dimethylformamide (75 ml) containing 15 drops of pyridine was heated at 180° C. for 5 hr. The hot mixture was poured into a mixture of ice (50 g) and conc. NH$_4$OH (50 ml). The resulting precipitate was collected, washed with water, dried and recrystallized from chloroform-ethyl acetate to afford 5.6 g of 5-cyano-6-methoxy-1-naphthalenecarboxylic acid methyl ester: mp 210°–211° C., NMR (CDCl$_3$)δ 3.95 (s, 3H), 4.15 (s, 3H). To a stirred solution of the latter ester (5.95 g, 24.66 mmoles) in 2-methoxyethanol (100 ml) at 20°–22° C., 4N aqueous NaOH solution (12.3 ml) was added. The reaction mixture was stirred at 20°–22° C. for 60 hr, diluted with water, cooled to 0° C. and rendered acidic with 1N aqueous HCl. The precipitate was collected and dried to yield 5.6 g of the title compound; mp>290° C.; NMR (DMSO-d$_6$) δ 4.1 (s, 3H), 8.1 (m, 5H).

EXAMPLE 1h 5-(Trifluoromethyl)-6-methoxy-1-naphthalenecarboxylic Acid (V, R$^3$=5—CF$_3$, R$^4$=6—CH$_3$O and R$^5$=H)

A mixture of 5-iodo-6-methoxy-1-naphthalenecarboxylic acid methyl ester (10.26 g, 30 mmoles, described in Example 1f), trifluoromethyl iodide (12 g, 61.2 mmoles), freshly prepared copper powder (5.7 g, prepared according to the procedure of R. Q. Brewster and T. Groening, "Organic Syntheses", Coll. Vol. II, John Wiley and Sons, New York, N.Y., U.S.A., 1948, p. 445) and pyridine (45 ml) was charged into a stainless steel autoclave. The vessel was shaken and heated at 120° C. for 20 hr and cooled to room temperature. The mixture was diluted with diethyl ether-ethyl acetate (1:1). The insoluble material was removed by filtration. The filtrate was washed with 1N aqueous HCl, water and dried (MgSO$_4$). The solvent was removed under reduced pressure. The residue was crystallized from ethanol to give 6.4 g of 5-(trifluoromethyl)-6-methoxy-1-naphthalenecarboxylic acid methyl ester; mp 79°-80° C.; NMR (CDCl$_3$) δ 3.95 (s, 6H), 8.00 (m, 5H). A mixture of the latter ester (6.3 g, 22 mmoles), 1N aqueous NaOH solution (34.12 ml) and methanol (100 ml) was stirred at 20°-22° C. for 4 hr. The mixture was adjusted to pH 7 with 1N aqueous HCl, methanol was removed from the mixture by distillation and the concentrated mixture was made acidic (pH 2) with 1N aqueous HCl. The resulting precipitate was collected and dried to yield 6 g of the title compound; mp 218°-219° C.; NMR (DMSO-d$_6$) δ 4.0 (s, 3H), 8.3 (m, 5H), 10.6 (broad, 1H).

EXAMPLE 1i

5-Bromo-6-[3-(trifluoromethyl)phenylmethoxy]-1-naphthalenecarboxylic Acid [V, R$^3$=5-Br, R$^4$=6-[(3—CF$_3$—C$_6$H$_4$)—CH$_2$O] and R$^5$=H]

A mixture of 5-bromo-6-methoxy-1-naphthalenecarboxylic acid (33.35 g, 0.11 moles, described in example 1b) in glacial acetic acid (460 ml) and 47% aqueous HBr(417 ml) was heated at reflux for 9 hr. The resulting precipitate was collected, washed with water and dried over P$_2$O$_5$ under reduced pressure. The precipitate was recrystallized from ethanol-water to give 21.45 g of 5-bromo-6-hydroxy-1-naphthalenecarboxylic acid; mp>225° C.; NMR (DMSO-d$_6$)δ 8.0 (m, 5H), 11.0 (broad, 1H), 12.6 (broad, 1H).

The latter acid (1.2 g, 4.5 mmoles) was suspended in dry dimethylformamide (DMF, 25 ml). Sodium hydride (0.43 g, 9.0 mmoles, 50% mineral oil suspension) was added in small portions to the stirred suspension. Stirring was continued until the evolution of hydrogen ceased. A solution of 3-(trifluoromethyl)-phenylmethyl chloride (2.63 g, 13.5 mmoles) in dry DMF (5 ml) was added dropwise and the mixture was heated to 50°-60° C. for 1 hr. The solvent was evaporated under reduced pressure to dryness. The residue was triturated with water. The solid was separated from the water by filtration. The collected solid was washed with hexane to remove residual mineral oil and then recrystallized from ethanol-water to give 1.7 g of 5-bromo-6-[(3-trifluoromethyl)phenylmethoxy]-1-naphthalenecarboxylic acid, 3-trifluoromethyl ester; mp 114°-115° C., IR (CHCl$_3$) 1715 cm$^{-1}$.

A mixture of the latter ester (1.7 g, 2.9 mmoles), methanol (20 ml) and 1N aqueous NaOH (4 ml) was stirred for 24 hr at 20°-22° C. Additional 1N aqueous NaOH was added and the mixture was stirred at 40° C. for 3 hr. The solvent was evaporated. The residue was dissolved in water and the solution made acidic. The resulting precipitate was collected, washed with water, dried and recrystallized from ethanol to give 1.0 g of the title compound; mp 229°-230° C.; NMR (DMSO-d$_6$) δ 5.5 (s, 2H), 8.1 (m, 9H), 10.5 (broad, 1H).

5-Bromo-6-(4-chlorophenylmethoxy)-1-naphthalenecarboxylic acid, NMR (DMSO-d$_6$) δ 5.4 (s, 2H), 7.7 (m, 9H), 11.0 (broad, 1H), is obtained by following the procedure of Example 1i but replacing 3-(trifluoromethyl)phenylmethyl chloride with an equivalent amount of 4-chlorophenylmethyl chloride.

EXAMPLE 1j 5-(Trifluoromethyl)-1-naphthalenecarboxylic Acid (V, R$^3$=5—CF$_3$ and R$^4$ and R$^5$=H)

A mixture of 5-iodo-1-naphthalenecarboxylic acid methyl ester [8.8 g, 28 mmoles, described by C. Seer and R. School, Justus Leibigs Ann. Chem., 398, 82 (1913)], trifluoromethyl iodide (12 g, 61.2 mmoles), freshly prepared copper powder (5.7 g, prepared according to the procedure of R. Q. Brewster and T. Groening, "Organic Syntheses", Coll. Vol. II, John Wiley and Sons, New York, N.Y., U.S.A., 1948, p. 445) and pyridine (45 ml) was charged into a stainless steel autoclave. The vessel was shaken and heated at 130° C. for 24 hr and cooled to room temperature. The mixture was filtered to remove insoluble material. The filtrate was washed with 1N aqueous HCl, water and brine, dried (MgSO$_4$) and concentrated to dryness. The residue was crystallized from methanol to give 4.3 g of 5-(trifluoromethyl)-1-naphthalenecarboxylic acid methyl ester, NMR (CDCl$_3$) δ 4.0 (s, 3H), 8.0 (m, 6H).

The ester (4.25 g, 16.72 mmoles) was suspended in methanol (100 ml). A 2N aqueous NaOH solution (16.72 ml, 2 equivalents) was added to the suspension. The mixture was stirred at 20°-22° C. for 18 hr. The resulting clear solution was adjusted to pH 8 with 1N aqueous HCl and concentrated under reduced pressure. The concentrate was adjusted to pH 3 with 1N aqueous HCl. The resulting precipitate was collected, washed with water and dried under reduced pressure to give the title compound; mp 206°-208° C.

EXAMPLE 2

N-[(5-Bromo-1-naphthalenyl)carbonyl]-N-methylglycine Methyl Ester (II, R$^1$ and R=CH$_3$, R$^3$=5-Br and R$^4$ and R$^5$=H)

Procedure A

A catalytic amount (5 drops) of dry DMF was added to a suspension of the starting material of formula V, 5-bromo-1-naphthalenecarboxylic acid [10 g, 39.8 mmoles, described by W. F. Short and H. Wang, J. Chem. Soc., 990 (1950)], in thionyl chloride (100 ml). The suspension was heated cautiously to reflux (caution: a vigorous reaction can occur). The mixture was refluxed for 20 min. The mixture was evaporated to dryness. Toluene was added to the solid residue and the mixture was evaporated to dryness. The residue was dissolved in pyridine (100 ml). The solution was cooled in an ice bath. Dry N-methylglycine methyl ester hydrochloride (11.1 g, 79.6 mmoles), a starting material of formula VI, was added portionwise to the cooled solution. The mixture was stirred for 2 hr at 20° C. and then heated at reflux for 1 hr. The pyridine was removed by evaporation. Water was added to the oily residue. The mixture was extracted with ethyl acetate (3×150 ml). The combined extracts were washed with 1N aqueous HCl solution, a saturated solution of sodium bicarbonate and brine. After drying over MgSO$_4$, the extract was treated with charcoal, filtered and evaporated. The residue was crystallized from diethyl ether or ethanol to give the title compound; mp 91°–92° C.; NMR (CDCl$_3$) δ 2.8 & 3.25 (2s, 3H), 3.6 & 3.85 (2s, 3H), 4.35 (broad, 2H), 7.75 (m, 6H); UVλmax (EtOH) 321 nm (ε775), 316 (1,110), 299 (6,660), 289 (9,250), 279 (7,400), 225 (66,600); Anal. Calcd: C, 53.59% H, 4.20% N, 4.17%; Found: C, 53.60% H, 4.27% N, 4.21%.

Procedure B

A mixture of the starting material of formula V, 5-bromo-1-naphthalenecarboxylic acid (12.8 g, 52 mmoles), and 1-hydroxybenzotriazole (HOBt, 7.0 g, 52 mmoles) in DMF (200 ml) was prepared. N,N'-dicyclohexylcarbodiimide (DCC, 10.6 g, 52 mmoles) in DMF (30 ml) was added to the mixture. The resulting mixture was stirred at 20° C. for 1 hr and then cooled to 0° C. N-Methylglycine methyl ester hydrochloride (7.25 g, 52 mmoles) and then N-ethylmorpholine (6.7 ml, 52 mmoles) were added to the cooled mixture. The mixture was stirred for 30 min at 0° C. and then for 18 hr at 20° C. Thereafter, the mixture was filtered and concentrated to dryness under reduced pressure. The residue was subjected to chromatography on 325 g of silica gel using ethyl acetate-hexane (1:1) as the eluant. The pure fractions were pooled to yield 10.5 g of product which was recrystallized from ethyl acetate to give the title compound, identical to the product of procedure A of this example.

EXAMPLE 3

N-[(5-Bromo-1-naphthalenyl)thioxomethyl]-N-methylglycine Methyl Ester (I, R$^1$ and R$^2$=CH$_3$, R$^3$=5-Br and R$^4$ and R$^5$=H)

To a stirred solution of N-[(5-bromo-1-naphthalenyl)-carbonyl]-N-methylglycine methyl ester (35.5 g, 106 mmoles, described in Example 2) in dry pyridine (100 ml), phosphorus pentasulfide (44.5 g, 200 mmoles) was added portionwise. The mixture was stirred and refluxed for 1.5 hr. and then poured into a liter of water at 50° to 80° C. (caution: evolution of copious quantities of H$_2$S). The mixture was allowed to cool to 20° to 22° C. (room temperature), filtered and the filtrate was extracted with ethyl acetate. The extract was washed with 1N aqueous HCl solution, brine, a saturated solution of sodium carbonate and brine, dried (MgSO$_4$), filtered and evaporated to dryness. The residue was recrystallized from ethanol-water (4:1) to give the title compound; mp 85°–86° C.; NMR (CDCl$_3$) δ 3.0 (s, 3H), 3.85 (s, 3H), 4.58 & 5.37 (2d, J=17, 2H), 7.1–8.3 (m, 6H); UVλmax (EtOH) 281 nm (ε14,480), 218 (14,480).

By following serially the procedures of Examples 2 and 3 and using the appropriate starting material of formula V instead of 5-bromo-1-naphthalenecarboxylic acid, other compounds of formula I in which R$^1$ and R$^2$ each is methyl are obtained. Examples of the latter compounds are listed as products in Tables I and II together with the appropriate starting material of formula V used for their preparation.

TABLE I

| EXAMPLE | STARTING MATERIAL OF FORMULA V (R$^5$ = H) R$^3$ | R$^4$ | PRODUCT:N—[(prefix listed below-1-NAPHTHALENYL)-THIOXOMETHYL]-N—METHYL-GLYCINE METHYL ESTER |
|---|---|---|---|
| 4 | 4-Br | H | 4-bromo; NMR (CDCl$_3$) δ 2.85 & 3.25 (2s, 3H), 3.6 & 3.85 (2,s 3H), 4.35 (m, 2H), 7.7 (m, 6H); IR (CHCl$_3$) 1730, 1620 cm$^{-1}$ |
| 5 | 8-Br | H | 8-bromo; IR(CHCl$_3$) 1730, 1480, 1380, 1080 cm$^{-1}$; NMR (CDCl$_3$) δ 3.0 (s, 3H), 3.8 (s, 3H), 3.65 (m, 2H), 7.5 (m, 6H) |
| 6 | 5-CH$_3$O | H | 5-methoxy; NMR (CDCl$_3$) δ 2.81 & 3.21 (2s, 3H), 3.58 & 3.80 (2s, 3H), 3.97 (s, 3H), 4.37 (broad, 2H), 6.80 (d, 1H), 7.40 (m, 4H), 8.27 (m, 1H); IR (CHCl$_3$) 1740, 1630, 1578 cm$^{-1}$ |
| 7 | 5-Me | H | 5-methyl; NMR (CDCl$_3$) δ 2.68 (s, 3H), 3.05 (3H), 3.85 (3H), 3.75 & 4.9 (m,2H), 7.6 (s, 6H) |
| 8 | 5-Br | 6-[CH$_3$(CH$_2$)$_4$O] | 5-bromo-6-pentyloxy; mp 80–83° C.; NMR (CDCl$_3$) δ 0.9 (t, J = 7Hz, 3H), 1.1–2.0 (broad, 2H), 3.0 (s, 3H), 3.8 (s, 3H), 4.1 (m, 2H), 7.1–8.5 (broad, 5H) |
| 9 | 5-CN | H | 5-cyano; NMR (CDCl$_3$) δ 3.00 (s, 3H), 3.85 (s, 3H), 4.45 & 5.45 (d, 2H), 7.18 (m, 6H) |
| 9a | 4-CN | H | 4-cyano; NMR (CDCl$_3$) δ 3.1 (s, 3H), 3.85 (s, 3H), 4.55 & 5.25 (2d, J = 17Hz, 2H), 7.0–8.4 (m, 6H) |
| 10 | 5-NO$_2$ | H | 5-nitro; mp 116–117° C. |
| 11 | 5-Cl | H | 5-chloro; mass spectrum, m/e: 307/309 (M$^+$), 274/276 (M$^+$—H, S), 248/246 (M$^+$—COOMe) |
| 12 | 5-Br | 6-CH$_3$O | 5-bromo-6-methoxy; mp 115–117° C.; NMR (CDCl$_3$) δ |

TABLE I-continued

| | STARTING MATERIAL OF FORMULA V ($R^5$ = H) | | PRODUCT:N—[(prefix listed below-1-NAPHTHALENYL)-THIOXOMETHYL]-N—METHYL- |
|---|---|---|---|
| EXAMPLE | $R^3$ | $R^4$ | GLYCINE METHYL ESTER |
| 13 | 5-Br | 6-CH$_3$ | 3.00 (s, 3H), 3.84 (s, 3H), 3.98 (s, 3H) 5-bromo-6-methyl; NMR (CDCl$_3$) δ 2.6 (s, 3H), 3.0 (s, 3H), 3.85 (s, 3H), 4.5 & 5.35 (d, J = 16.5Hz, 2H), 7.7 (m, 5H) |
| 14 | H | H | *; IR (CHCl$_3$) 1735 cm$^{-1}$ |
| 15 | 4-Cl | H | 4-chloro; mp 100–101° C.; NMR (CDCl$_3$) δ 3.10 & 3.62 (2s, 3H); 3.90 & 3.70 (2s, 3H) 4.04, 4.55 & 5.37 (s, 2d, J = 16Hz, 2H), 7.2–8.4 (m, 6H); IR (CHCl$_3$) 1740 cm$^{-1}$; UVλmax (EtOH) 283 nm (ε7,100), 219 (52,000); Anal. Calcd: C, 58.54% H, 4.58% N, 4.55%; Found: C, 58.58% H, 4.76% N, 4.58% |
| 16 | 3-Cl | 4-CH$_3$O | 3-chloro-4-methoxy; mp 85–86° C.; NMR (CDCl$_3$) δ 3.05 (s, 3H), 3.85 (s, 3H), 4.00 (s, 3H), 4.58 & 5.3 (2d, J = 17Hz, 2H), 7.6 (m, 5H) |
| 17 | 5-Cl | 7-Cl | 5,7-dichloro; m/e; 325/327/329 (M$^+$), 266, 268, 270 (M$^+$—COOCH$_3$), 223/225/227 (M$^+$—CH$_3$—N—CH$_2$—COOCH$_3$) |
| 18 | 5-I | 6-CH$_3$O | 5-iodo-6-methoxy; mp 149–150° C.; NMR (CDCl$_3$) δ3.00 (s, 3H), 3.85 (s, 3H), 3.95 (s, 3H), 4.4 & 5.45 (d, 2H), 7.6 (m, 5H) |
| 19 | 5-CN | 6-CH$_3$O | 5-cyano-6-methoxy; mp 164–165° C.; NMR (CDCl$_3$) δ 3.05 (s, 3H), 3.90 (s, 3H), 4.07 (s, 3H), 4.35 & 5.55 (d, J = 16.8Hz, 2H), 7.80 (m, 5H) |

*No prefix as compound is N—((1-naphthalenyl)thioxomethyl)-N—methylglycine methyl ester With reference to Table I, the starting materials of formula V are described by T. L. Jacobs, et al., J. Org. Chem., 11, 27 (1946) for example 4; by H. G. Rule et al., J. Chem. Soc., 168 (1934) for example 5; by A. Girardet and N. Lorusso, Helv. Chim. Acta., 49, 471 (1966) for example 6; by M. J. S. Dewar and P. J. Grisdale, J. Am. Chem. Soc., 84, 3541 (1962) for example 7; in example 1c for example 8; by M. J. S. Dewar and P. J. Grisdale, J. Am. Chem. Soc., 84, 3541 (1962) for examples 9, 9a, 10 and 11; in example 1b for example 12; in example 1c for example 13; by H. Gilman et al., "Organic Syntheses", Coll. Vol. II, John Wiley and Sons, New York, N.Y., U.S.A., 1948, p. 425 for example 14; by T. L. Jacobs et al., J. Org. Chem., 11 27 (1946) for example 15; in example 1d for example 16; in example 1e for example 17; in example 1f for example 18; and in example 1g for example 19.

TABLE II

| | STARTING MATERIAL OF FORMULA V ($R^5$ = H) | | PRODUCT:N—[[prefix listed below-1-NAPHTHALENYL]-THIOXOMETHYL]-N—METHYL- |
|---|---|---|---|
| EXAMPLE | $R^3$ | $R^4$ | GLYCINE METHYL ESTER |
| 20 | 5-Br | 6-[CH$_3$O(CH$_2$)$_3$O] | 5-bromo-6-(3-methoxypropoxy); NMR (CDCl$_3$) δ 2.1 (m, 4H), 3.35 (s, 6H), 3.55 (m, 4H), 4.25 (t, J = 6Hz, 2H), 4.45 (t, 5 = 6Hz, 2H), 7.4 (m, 2H), 8.0 (d, J = 8Hz, 1H), 8.4 (d, J = 8Hz, 1H), 8.85 (d, J = 8Hz, 1H) |
| 21 | 5-[CH$_2$=C(CH$_3$)] | H | 5-(1-methylethenyl); mp 93–95° C.; NMR (CDCl$_3$) δ 2.15 (s, 3H), 3.05 (s, 3H), 3.85 (s, 3H), 4.55 & 5.3 (2s, 2H), 5.0 & 5.35 (2s, 2H), 7.6 (m, 6H) |
| 22 | 5-[(CH$_3$)$_2$CH] | H | 5-(1-methylethyl); NMR (CDCl$_3$) δ 1.35 (m, 6H), 3.0 & 3.55 (2s, 3H), 3.65 & 3.85 (2s, 3H), 4.95 (2H), 7.5 (m, 6H) |
| 23 | 5-CF$_3$ | 6-CH$_3$O | 5-(trifluoromethyl)-6-methoxy; mp 109–110° C.; NMR (CDCl$_3$) δ 3.00 (s, 3H), 3.85 (s, 3H), 3.95 (s, 3H), 4.35 & 5.45 (d, 2H), 7.7 (m, 5H) |

TABLE II-continued

| EXAMPLE | STARTING MATERIAL OF FORMULA V ($R^5$ = H) | | PRODUCT:N—[[prefix listed below-1-NAPHTHALENYL]-THIOXOMETHYL]-N—METHYL-GLYCINE METHYL ESTER |
|---|---|---|---|
| | $R^3$ | $R^4$ | |
| 24 | 5-Br | 6-[(3-CF$_3$—C$_6$H$_4$)—CH$_2$O] | 5-bromo-6-[3-(trifluoromethyl)-phenylmethoxy]; NMR (CDCl$_3$) δ 3.00 (s, 3H), 3.85 (s, 3H), 4.4 & 5.4 (2d, J = 16.5Hz, 2H), 5.25 (s, 2H), 7.6 (m, 9H) |
| 24a | 5-Br | 6-[(4-Cl—C$_6$H$_4$)—CH$_2$O] | 5-bromo-6-(4-chlorophenyl-methoxy); NMR (CDCl$_3$) δ 3.00 (s, 3H), 3.85 (s, 3H), 4.40 & 5.40 (d, 2H), 5.2 (s, 2H), 7.5 m 9H) |
| 24b | 5-CF$_3$ | H | 5-(trifluoromethyl); NMR (CDCl$_3$) δ 3.00 (s, 3H), 3.85 (s, 3H), 4.5 & 5.4 (d, 2H), 7.2-8.3 (m, 6H). |

With reference to Table II, the starting materials of formula V are described in example 1; herein, for example 20; in example 1 for example 21; in example 1a for example 22; in example 1h for example 23; in example 1i for example 24 and example 24a; and in example 1j for example 24b.

By following serially the procedures of examples 2 and 3, but using the appropriate starting material of formula VI instead of N-methylglycine, other compounds of formula I in which $R_2$ is lower alkyl, $R^3$ is 5-bromo, $R^4$ is hydrogen are obtained. Examples of the latter compounds are listed as products in Table III together with the appropriate starting material of formula VI used for their preparation.

TABLE III

| EXAMPLE | STARTING MATERIAL OF FORMULA VI | | PRODUCT:N—[(5-BROMO-1-NAPHTHALENYL)THIOXOMETHYL]-suffix listed below |
|---|---|---|---|
| | $R^1$ | R | |
| 25 | H | CH$_3$ | glycine methyl ester; mp 126–130° C.; NMR (CDCl$_3$) δ 3.8 (s, 3H), 4.6 (d, J = 7Hz, 2H), 7.15-8.15 (m, 6H) |
| 26 | n-C$_3$H$_7$ | C$_2$H$_5$ | N—propylglycine ethyl ester; NMR (CDCl$_3$) δ 0.65 (t, J = 7Hz, 3H), 1.4 (t, 3H), 1.45 (m, 2H), 3.2 (t, J = 7Hz, 2H), 4.3 (q, J = 7Hz, 2H), 4.35 (d, J = 17Hz, 1H), 5.3 (d, J = 17Hz, 1H), 7.7 (m, 6H); IR (CHCl$_3$) 1740 cm$^{-1}$ |
| 27 | CH$_2$=CH—CH$_2$ | CH$_3$ | N—(2-propenyl)glycine methyl ester; mp 72–74° C. |
| 28 | C$_2$H$_5$ | CH$_3$ | N—ethylglycine methyl ester; NMR (CDCl$_3$) δ 1.10 (t, 3H), 3.35 (q, 2H), 3.85 (s, 3H), 4.40 & 5.25 (d, 2H), 7.6 (m, 6H) |
| 29 | n-C$_4$H$_9$ | C$_2$H$_5$ | N—butylglycine ethyl ester; NMR (CDCl$_3$) δ 0.65 (t, J = 5.5 Hz, 3H), 1.0 (m, 2H), 1.38 (t, 3H), 1.40 (m, 2H), 3.25 (m, 2H), 4.25 & 5.30 (d, J = 16Hz, 2H), 7.7 (m, 6H) |
| 30 | C$_6$H$_5$CH$_2$ | C$_2$H$_5$ | N—(phenylmethyl)glycine ethyl ester; mp 141–142° C.; NMR (CDCl$_3$) δ 1.35 (t, J = 7Hz, 3H), 4.50 (m, 6H), 7.50 (m, 11H); IR(Nujol*) 1743 cm$^{-1}$ |

*Trademark

EXAMPLE 31

By following serially the procedure of Examples 2 and 3, but using the appropriate starting material of formula V and the appropriate aminoacid ester of formula VI, still other compounds of formula I in which $R^2$ is lower alkyl are obtained. For example, by using 3-chloro-4-methoxy-1-naphthalenecarboxylic acid, described in Example 1d, as the starting material of formula V, and using glycine ethyl ester hydrochloride as the starting material of formula VI, N-[(3-chloro-4-methoxy-1-naphthalenyl)thioxomethyl]glycine ethyl ester; IR (CHCl$_3$) 3420, 3340, 1740, 1665 cm$^{-1}$; via N[(3-chloro-4-methoxy-1-naphthalenyl)carbonyl]glycine ethyl ester; mp 140°–141° C.; NMR (CDCl$_3$) δ 1.3 (t, J=7Hz, 3H), 4.2 (m, 4H), 6.55 (broad, 1H), 7.55 (m, 3H), 8.2 (m, 2H), was obtained.

EXAMPLE 32

N-[(5-Bromo-1-naphthalenyl)thioxomethyl]-N-methylglycine (I, $R^1$=CH$_3$, $R^2$, $R^4$ and $R^5$=H and $R^3$=5-Br)

A 1N aqueous NaOH solution (25 ml) was added to a suspension of N-[(5-bromo-1-napthalenyl)thioxomethyl]-N-methylglycine methyl ester (7.3 g, 20.7 mmoles;

described in Example 3) in methanol (75 ml). The mixture was stirred at 20° to 22° C. for 2½ hr, neutralized to pH 7 with aqueous HCl and concentrated under reduced pressure to remove methanol. The residual solution was rendered acidic (pH=2) with the addition of aqueous HCl solution and extracted with ethyl acetate. The extract was dried (MgSO$_4$) and evaporated to dryness. The residue was crystallized from ethyl acetate-hexane to give 5.3 g of the title compound; mp 181° C.; NMR (DMSO-d$_6$) δ 2.95 (s, 3H), 4.65 & 5.2 (2d, J=16.8, 2H), 7.85 (m, 6H), UVλmax (EtOH) 285 nm (ε12,300), 280 (12,400), 221 (42,600); IR(Nujol TM) 2900, 1720 cm$^{-1}$; Anal Calcd: C, 49.72% H, 3.58% N, 4.14%; Found: C, 49.63% H, 3.63% N, 4.18%.

In the same manner, but replacing N-[(5-bromo-1-naphthalenyl)thioxomethyl]-N-methylglycine methyl ester with an equivalent amount of N-[(3-chloro-4-methoxy-1-naphthalenyl)thioxomethyl]glycine ethyl ester, described in Example 31, N-[(3-chloro-4-methoxy-1-naphthalenyl)thioxomethyl]glycine [mp 217° C.(dec); NMR(DMSO-d$_6$) δ 3.96 (s, 3H), 4.42 (d, J=6 Hz, 2H), 7.40 (s, 1H), 7.65 (m, 2H), 8.18 (m, 2H); IR (Nujol TM) 3150, 2900, 1720, 1140 cm$^{-1}$; UVλmax (EtOH) 277 nm (ε11,400), 224 (51,300); Anal Calcd: C, 54.28% H, 3.91% N, 4.52%; Found: C, 54.26% H, 4.06% N, 4.62%] was obtained.

By following the procedure of Example 32, but replacing N-[(5-bromo-1-naphthalenyl)thioxomethyl]-N-methylglycine methyl ester with an equivalent amount of another ester compound of formula I in which R$^2$ is lower alkyl, or a corresponding compound of formula III in which R is ar(lower)alkyl, the corresponding compound of formula I in which R$^2$ is hydrogen was obtained. Examples of the latter compounds are listed as products in Tables IV, V and VI together with a notation to the corresponding compound of formula I in which R$^2$ is lower alkyl from which they are prepared. In each case the compound of formula I in which R$^2$ is lower alkyl, the starting material, is noted by the example in which it was prepared.

TABLE IV

| EXAMPLE | NO. OF THE EXAMPLE IN WHICH STARTING MATERIAL WAS PREPARED | PRODUCT:N—[(prefix listed below-1-NAPHTHALENYL)-THIOXOMETHYL]-N—METHYL-GLYCINE |
|---|---|---|
| 33 | 4 | 4-bromo; mp 168–169° C. NMR(DMSO-d$_6$) δ 3.0 (s, 3H), 4.65 & 5.15 (d, J = 16.5Hz, 2H), 7.7 (m, 6H); Anal Calcd: C, 49.71% H, 3.58% N, 4.14%; Found: C, 49.56% H, 3.42% N, 4.22% |
| 34 | 5 | 8-bromo; mp 65–85° C.; Anal Calcd: C, 49.72% H, 3.58% N, 4.14%; Found: C, 53.54% H, 4.05% N, 4.40% |
| 35 | 6 | 5-methoxy; mp 120° C.; NMR(DMSO-d$_6$) δ 2.93 (s, 3H), 3.90 (s, 3H), 4.65 & 5.16 (2d, J = 17Hz, 2H), 6.95 (2d, J$_1$ = 7Hz, J$_2$ = 3Hz, 1H), 7.35 (m, 4H), 8.11 (2d, J$_1$ = 8Hz, J$_2$ = 2Hz, 1H); IR(Nujol*) 2900, 1734, 1715 cm$^{-1}$; UVλmax EtOH) 281 nm(ε 11,600), 233 (30,600); Anal Calcd: C, 62.27% H, 5.23% N, 4.84%; Found: C, 61.62% H, 5.95% N, 4.22% |
| 36 | 7 | 5-methyl; mp 190–191° C., NMR(CDCl$_3$) δ 2.66 (s, 3H), 3.05 (s, 3H), 3.85 & 5.0 (m, 2H), 7.5 (m, 6H), 8.75 (broad,) 1H); IR(CHCl$_3$) 3000, 1755 1720 cm$^{-1}$; UVλmax (EtOH) 282 nm (ε15,280), 226 (39,690), 218 (41,385); Anal Calcd: C, 65.90% H, 5.53% N, 5.12%; Found: C, 65.79% H, 5.57% N, 5.08% |
| 37 | 8 | 5-bromo-6-pentyloxy; mp 211–217° C.; NMR(DMSO-d$_6$) δ 0.9 (t, J = 6Hz, 3H), 1.6 (m, 2H), 2.9 (s, 3H), 4.2 (t, J = 6Hz, 2H), 3.95 & 5.15 (d, J = 15Hz, 2H), 7.1–8.55 (m, 5H); IR(Nujol*) 3000, 1650 cm$^{-1}$ |
| 38 | 9 | 5-cyano; mp 190–200° C.; NMR (DMSO-d$_6$) δ 3.00 (s, 3H), 4.65 & 5.15 (d, J = 17Hz, 2H), 7.95 (m, 6H); IR(Nujol*) 3000, 2230, 1730 cm$^{-1}$; UVλmax (EtOH) 313 nm (ε5,600), 271 (13,850), 249 (14,620), 222 (48,340); Anal Calcd: C, 63.36% H, 4.34% N, 9.85%; Found: C, 62.01% H, 4.34% N, 9.36% |
| 38a | 9a | 4-cyano; mp 192–193° C.; NMR (DMSO-d$_6$) δ 3.0 (s, 3H), 4.7 |

TABLE IV-continued

| EXAMPLE | NO. OF THE EXAMPLE IN WHICH STARTING MATERIAL WAS PREPARED | PRODUCT:N—[(prefix listed below-1-NAPHTHALENYL)-THIOXOMETHYL]-N—METHYL-GLYCINE |
|---|---|---|
| | | & 5.2 (d, J = 17Hz, 2H), 7.8 (m, 6H), 10.05 (broad, 1H); IR (Nujol*) 3180, 2230, 1745 (with inflection at 1755)cm$^{-1}$ |
| 39 | 10 | 5-nitro; mp 142–143° C.; NMR (CDCl$_3$) δ 3.05 (s, 3H), 4.65 & 5.4 (d, 2H), 7.9 (m, 6H), 9.4 (broad, 1H); IR(Nujol*) 2900, 1715, 1530, 1345 cm$^{-1}$; UVλmax (EtOH) 332 nm (ε 4,110) 269 (17,010); Anal Calcd: C, 55.26% H, 3.96% N, 9.20%; Found: C, 55.17% H, 3.86% N, 9.10% |
| 40 | 11 | 5-chloro; mp 153–154° C.; NMR(CDCl$_3$) δ 3.03 (s, 3H), 4.67 & 5.33 (d, J = 17Hz, 2H), 7.50 (m, 4H), 7.90 (d, J = 8Hz, 1H), 8.25 (d, J = 8, 1H); IR(CHCl$_3$) 3000, 1720 cm$^{-1}$; UVλmax (EtOH) 280 nm (ε 16,780), 212 (52,290); Anal Calcd: C, 57.23% H, 4.12% N, 4.77%; Found: C, 58.02% H, 4.28% N, 4.94% |
| 41 | 12 | 5-bromo-6-methoxy; mp 166–168° C.; NMR(CDCl$_3$) δ 3.02 (s, 3H), 4.06 (s, 3H), 4.61 & 5.39 (d, J = 17Hz, 2H); IR(CHCl$_3$) 3000, 1718 cm$^{-1}$; UVλmax (EtOH) 341 nm (4,350), 329 (4,015), 273 (13,150), 237 (51,260); Anal Calcd: C, 48.92% H, 3.83% N, 3.80%; Found: C, 49.11% H, 3.90% N, 3.91% |
| 42 | 13 | 5-bromo-6-methyl; mp 190–192° C.; NMR(CDCl$_3$) δ 2.6 (s, 3H), 3.05 (s, 3H), 4.56 & 5.3 (d, 2H), 7.6 (m, 5H); IR(CHCl$_3$) 3000, 1720 cm$^{-1}$; UVλmax (EtOH) 280 nm (ε 14,055), 223 (43,400); Anal Calcd: C, 51.14% H, 4.01% N, 3.98%; Found: C, 51.21% H, 4.03% N, 4.00% |
| 43 | 14 | *; mp 146–147° C.; NMR(CDCl$_3$) δ 3.05 & 3.70 (2s, 3H), 4.07, 4.75 & 5.30 (s, 2d, J = 17Hz, 2H), 6.8–8.0 (m, 7H), 9.20 (broad, 1H); IR(CHCl$_3$) 3000, 1720 (inflection at 1755)cm$^{-1}$; UVλmax (EtOH) 280 nm (ε 14,415), 215 (53,450); Anal Calcd: C, 64.87% H, 5.05% N, 5.40%; Found: C, 64.89% H, 5.14% N, 5.51% |
| 44 | 15 | 4-chloro; mp 165–166° C.; NMR(CDCl$_3$) δ 3.05 & 3.70 (2s, 3H), 4.10, 4.70 & 5.3 (s, 2d, J = 17Hz, 2H), 7.2–8.4 (m, 6H), 10.5 (s, 1H), IR(CHCl$_3$) 3000, 1725 (with inflection at 1765)cm$^{-1}$; UVλmax(EtOH) 283 nm (ε13,500), 220 (49,600); Anal Calcd; C, 57.24% H, 4.12% N, 4.77%; Found: C, 57.56% H, 4.28% N, 4.84% |
| 45 | 16 | 3-chloro-4-methoxy; mp 138–139° C.; NMR(DMSO-d$_6$) δ 3.0 (s, 3H), 3.45 (s, 3H), 4.6 & 5.15 (2d, J = 16.8Hz, 2H), 7.3 (s, 1H), 7.8 (m, 4H); IR(Nujol*)2900, 1723 cm$^{-1}$; UVλmax (EtOH) 329 nm (ε 2,200), 282 (13,210), 224 (53,980); Anal Calcd: C, 55.64% H, 4.36% N, 4.33%; Found: C, 55.63% H, 4.48% N, 4.40% |

TABLE IV-continued

| EXAMPLE | NO. OF THE EXAMPLE IN WHICH STARTING MATERIAL WAS PREPARED | PRODUCT:N—[(prefix listed below-1-NAPHTHALENYL)-THIOXOMETHYL]-N—METHYL-GLYCINE |
|---|---|---|
| 46 | 17 | 5,7-dichloro; mp 174–175° C.; NMR(DMSO-d$_6$) δ 2.97 (3H), 4.57 & 5.27 (2d, J = 17Hz, 2H), 7.3–8.3 (m, 5H); IR(Nujol*) 3000, 1708 cm$^{-1}$; UVλmax (EtOH) 334 nm (ε3,050), 273 (15,810), 226 (63,800); Anal Calcd: C, 51.23% H, 3.38% N, 4.27%; Found: C, 51.44% H, 3.52% N, 4.40% |
| 47 | 18 | 5-iodo-6-methoxy; mp 161–163° C.; NMR(DMSO-d$_6$) δ 2.95 (s, 3H), 3.95 (s, 3H), 4.6 & 5.2 (d, J = 17Hz, 2H), 7.5 (m, 5H); IR (Nujol*) 2900, 1720 cm$^{-1}$; UVλmax (EtOH) 343 nm (ε 7,900), 333 (7,250) 308 (12,400), 273 (20,500), 240 (74,200); Anal Calcd: C, 43.39% H, 3.40% N, 3.37%; Found: C, 42.75% H, 3.35% N. 3.37% |
| 48 | 19 | 5-cyano-6-methoxy; mp 155–157° C.; NMR(CDCl$_3$) δ 3.05 (s, 3H), 4.05 (s, 3H), 4.55 & 5.45 (d, J = 17Hz, 2H), 7.7 (m, 5H); IR(CHCl$_3$) 2900, 2220, 1725 cm$^{-1}$; UVλmax (EtOH) 346 nm (ε 5,600), 339 (5,500), 232 (46,500) |

*Trademark
*No prefix as compound is N—((1-naphthalenyl)thioxomethyl)-N—methylglycine

TABLE V

| EXAMPLE | NO. OF THE EXAMPLE IN WHICH STARTING MATERIAL WAS PREPARED | PRODUCT:N—[[prefix listed below-1-NAPHTHALENYL]-THIOXOMETHYL]-N—METHYL-GLYCINE |
|---|---|---|
| 49 | 20 | 5-bromo-6-(3-methoxy-propoxy); NMR(CDCl$_3$) δ 2.1 (q, J = 6Hz, 2H), 3.0 (s, 3H), 3.35 (s, 3H), 3.65 (t, J =6Hz, 2H), 4.25 (t, J = 6Hz, 2H), 4.55 (d, J = 16Hz, 1H), 5.4 (d, J = 16Hz, 1H), 7.4 (m, 3H), 7.95 (d, J = 8Hz, 1H), 8.2 (d, J = 8Hz, 1H); IR(CHCl$_3$) 2900, 1720 cm$^{-1}$; UVλmax (EtOH) 341 nm (ε 3,920), 330 (3,730), 238 (49,400); Anal Calcd: C, 50.69% H, 4.73% N, 3.29%; Found: C, 50.29% H, 4.89% N, 3.23% |
| 50 | 21 | 5-(1-methylethenyl); mp 146–148° C.; NMR(CDCl$_3$) δ 2.2 (s, 3H), 3.1 (s, 3H), 4.75 & 5.35 (d, 2H), 5.05 & 5.4 (d, 2H), 7.6 (m, 6H), 8.5 (broad, 1H); IR(CHCl$_3$) 2900, 1760, 1720 cm$^{-1}$; UVλmax (EtOH) 282 nm (ε 14,000), 216 (38,900); Anal Calcd: C, 68.20% H, 5.72% N, 4.68%, C, 69.06% H, 6.03% N, 4.39% |
| 51 | 22 | 5-(1-methylethyl); mp 136–136° C.; NMR(CDCl$_3$) δ 1.40 (m, 6H), 3.05 & 3.65 (d, 3H), 3.65 (m, 1H), 5.05 (m, 2H), 7.5 (m, 6H), 9.60 (broad, 1H); IR(CHCl$_3$) 2900, 1755, 1720 cm$^{-1}$; Anal Calcd: C, 67.74% H, 6.35% N, 4.65%; Found: C, 66.44% H, 6.55% N, 4.16% |
| 52 | 23 | 5-(trifluoromethyl)-6-methoxy; mp 164–165° C.; NMR(CDCl$_3$) |

TABLE V-continued

| EXAMPLE | NO. OF THE EXAMPLE IN WHICH STARTING MATERIAL WAS PREPARED | PRODUCT:N—[[prefix listed below-1-NAPHTHALENYL]-THIOXOMETHYL]-N—METHYL-GLYCINE |
|---|---|---|
| 53 | 24 | δ 3.05 (s, 3H), 3.95 (s, 3H), 4.55 & 5.4 (d, J = 17Hz, 2H), 7.6 (m, 5H), 9.8 (broad, 1H); IR(CHCl$_3$) 2900, 1720 cm$^{-1}$; UVλmax (EtOH) 337 nm (ε 3,895), 268 (13,260), 226 (49,315); Anal Calcd: C, 53.78% H, 3.95% N, 3.92%; Found: C, 53.56% H, 3.95% N, 3.87% |
| 53b | | 5-bromo-6-(3-trifluoromethyl)-phenylmethoxy]; mp 125° C.; NMR(DMSO-d$_6$) δ 3.0 (s, 3.70% N, 4.27% Found: C, 54.69% H, 3.70% N, 4.27% |

TABLE VI

| EXAMPLE | NO. OF THE EXAMPLE IN WHICH STARTING MATERIAL WAS PREPARED | PRODUCT:N—[(5-BROMO-1-NAPHTHALENYL)THIOXO-METHYL]-suffix listed below |
|---|---|---|
| 54 | 25 | glycine; mp 232–237° C.; NMR (DMSO-d$_6$) δ 4.5 (d, J = 5.5, 2H), 7.8 (m, 6H), 10.8 (broad, 1H); IR(Nujol*)3200, 1720; UVλmax (EtOH) 275 nm (ε 11,700), 217 (44,800); Anal Calcd C, 48.15% H, 3.10% N, 4.30%; Found: C, 48.65% H, 3.18% N, 4.37% |
| 55 | 26 | N—propylglycine; NMR(CDCl$_3$) δ 0.65 (t, J = 8Hz, 3H), 1.55 (sextet, J = 8Hz, 2H), 3.25 (t, J = 8Hz, 3H), 4.55 (d, J = 17Hz, 1H), 5.3 (d, J = 17Hz, 1H), 7.7 (m, 6H); IR(CHCl$_3$) 2900, 1723 cm$^{-1}$; UVλmax (EtOH) 277 nm (ε 14,800), 216 (61,200); Anal Calcd: C, 52.44% H, 4.41% N, 3.83%; Found: C, 52.53% H, 4.44% N, 3.73% |
| 56 | 27 | N—(2-propylene)glycine: NMR (CDCl$_3$) δ 3.5 (m, 2H), 3.9 (m, 2H), 5.4 (m, 3H), 6.95 (m, 1H), 7.2–8.4 (m, 6H); IR (CHCl$_3$) 2900, 1720 with inflection at 1760 cm$^{-1}$; UVλmax (EtOH) 277 nm (ε 14,400), 219 (39,700); Anal Calcd: C, 52.76% H, 3.87% N, 3.84%; Found: C, 52.93% H, 4.28% N, 3.68% |
| 57 | 28 | N—ethylglycine; mp 182–184° C.; NMR(DMSO-d$_6$) δ 0.95 (t, J = 7Hz, 3H), 3.25 (q, J = 7Hz, 2H), 4.58 & 5.05 (d, J = 16.5Hz, 2H), 7.7 (m, 6H); IR (Nujol*) 2900, 1720 cm$^{-1}$; UVλmax (EtOH) 276 nm (ε 14,795), 219 (42,305); Anal Calcd: C, 51.14% H, 4.00% N, 3.97%; Found: C, 51.33% H, 4.08% N, 4.05% |
| 58 | 29 | N—butylglycine; mp 65–68° C. (dec); NMR(CDCl$_3$) δ 0.63 (t, J = 5.5Hz, 3H), 1.2 (m, 4H), 3.25 (t, J = 7.5Hz, 2H), 4.5 & 5.3 (d, J = 16.8Hz, 2H), 6.9 (broad, 1H), 7.7 (m, 6H); IR(CHCl$_3$) 2900, 1720 cm$^{-1}$; UVλmax (EtOH) 378 nm (ε 13,900), 219 (42,000) |
| 59 | 30 | N—(phenylmethyl)glycine; mp 98° C.(decomp); NMR(CDCl$_3$) δ 4.5 & 5.35 (d, 2H), 4.45 (m, 2H), 7.6 (m, 11H); IR(Nujol*) 2900, 1710 cm$^{-1}$; UVλmax |

TABLE VI-continued

| EXAMPLE | NO. OF THE EXAMPLE IN WHICH STARTING MATERIAL WAS PREPARED | PRODUCT:N—[(5-BROMO-1-NAPHTHALENYL)THIOXO-METHYL]-suffix listed below |
|---------|---|---|
| | | (EtOH) 278 nm (15,620), 219 (43,465); Anal Calcd: C, 58.01% H, 3.94% N, 3.35%: Found: C, 58.29% H, 4.27% N, 3.24% |

*Trademark

EXAMPLE 60

N-[(5-Bromo-1-naphthalenyl)carbonyl]-N-methylglycine (IV, $R^1=CH_3$, $R^3=$5-Br and $R^4$ and $R^5=H$)

N-[(5-Bromo-1-naphthalenyl)carbonyl]-N-methylglycine methyl ester (3.7 g, 11.0 mmoles, described in Example 2) was suspended in methanol (50 ml). A solution of 1N aqueous NaOH (13.2 ml) was added to the suspension. The mixture was stirred at 20°–22° C. for 1.5 hr. The mixture was neutralized with aqueous HCl and concentrated under reduced pressure to remove the methanol. The residual solution was made acidic with aqueous HCl and extracted with ethyl acetate. The extract was dried (MgSO$_4$), filtered and evaporated to dryness. The residue was crystallized from ethanol-water to give 3.25 g of the title compound; mp 205° C.; NMR (DMSO-d$_6$) δ 2.75 & 3.10 (2s, 3H), 2.75 & 3.10 (2s, 3H), 3.75 & 4.25 (2s, 2H), 7.3–8.3 (m, 6H); IR (Nujol ™ ) 1745 with inflection at 1720, 1580 cm$^{-1}$; UVλmax (EtOH) 322 nm (ε680), 316 (1,000), 299 (6,510), 289 (9,055), 279 (7,150) 226 (63,080); Anal Calcd: C, 52.19% H, 3.76% N, 4.35%; Found: C, 52.09% H, 38.4% N, 4.48%.

By following the procedure of example 60 but replacing N-[(5-bromo-1-naphthalenyl)carbonyl]-N-methylglycine methyl ester with an equivalent amount of another ester compound of formula II in which R is lower alkyl as ar(lower)alkyl, the corresponding compound of formula IV is obtained. For example, replacement with N-[[5-(trifluoromethyl)-6-methoxy-1-naphthalenyl]carbonyl]-N-methylglycine methyl ester, NMR (CDCl$_3$) ε 2.85 (s, 3H), 3.5–4.5 (m, 2H), 3.4 & 3.75 (2s, 6H), 7.0–8.4 (m, 5H), prepared according to the procedure of example 2, gives N-[[5-(trifluoromethyl)-6-methoxy-1-naphthanenyl]carbonyl]-N-methylglycine, mp 174°–175° C.; NMR (DMSO-d$_6$) δ 2.75 & 3.1 (2s, 3H), 4.03 (s, 3H), 4.30 (d, 2H), 7.8 (m, 5H); IR (Nujol ™ ) 2500, 1720 with inflection at 1745, 1580 cm$^{-1}$; UVλmax (EtOH) 335 nm (ε3,050), 322 (2,700), 295 (5,100), 283 (5,750), 275 (4,450), 220 (57,100); Anal Calcd: C, 56.30% H, 4.13% N, 4.10%; Found: C, 55.29% H, 4.02% N, 3.99%.

EXAMPLE 61

4,6-Dimethoxy-1-naphthalenecarboxylic Acid (V, $R^3=$4—$CH_3O$, $R^4=$6—$CH_3O$ and $R^5=H$)

A stream of chlorine gas was passed through a cooled solution of NaOH (17.28 g, 0.432 mole) in water (24 ml) containing 100 g of ice until 12.7 g (0.18 mole) of chlorine was absorbed into the solution. Solid (4,6-dimethoxy-1-naphthalenyl)ethanone [9.2 g, 0.04 mole, described by N. P. Buu-Hoï, J. Org. Chem., 21, 1257 (1956)], was added at 20°–22° C. to the chlorine solution. The mixture was stirred at 65° C. for one hr, cooled in an ice bath and treated with NaHSO$_3$ (5 g) in water (20 ml). The mixture was made neutral by the addition of dilute HCl. The resulting precipitate was collected, washed well with water, dried over P$_2$O$_5$ and recrystallized from methanol to give 4,6-dimethoxy-1-naphthalenecarboxylic acid (7.0 g); mp 227°–229° C.; NMR (DMSO-d$_6$) δ 3.85 (s, 3H), 4.0 (s, 3H), 7.7 (m, 5H); IR (white mineral oil) 2900, 1670 cm$^{-1}$; UVλmax (MeOH) 339 nm (ε4,910), 328 (4500), 304 (8,180), 240 (40,100); Anal Calcd: C, 67.23% H, 5.21%; Found: C, 67.15% H, 5.23%.

EXAMPLE 62

4,6-Dimethoxy-5-(trifluoromethyl)-1-naphthalenecarboxylic Acid (V, $R^3=$4—$CH_3O$, $R^4=$5—$CF_3$ and $R^5=$6—$CH_3O$)

4,6-Dimethoxy-1-naphthalenecarboxylic acid (98.5 g, 0.425 mole, described in Example 61) was added to an ice-cooled solution of SOCl$_2$ (59.5 g, 0.5 mole) in anhydrous methanol (225 ml). The mixture was heated at reflux for 18 hr. Another portion of SOCl$_2$ (35.5 ml) was added and the reflux was continued for another 7 hr. The mixture was extracted with diethyl ether. The ether extract was washed with water and then aqueous NaHCO$_3$ solution, dried (Na$_2$SO$_4$) and concentrated to dryness. The solid residue was crystallized from methanol (720 ml) to give 64.5 g of 4,6-dimethoxy-1-naphthalenecarboxylic acid methyl ester; mp 102°–104° C.; NMR (CDCl$_3$) δ3.9 (s, 6H), 4.0 (s, 3H), 7.7 (m, 5H).

The latter compound (4.93 g, 0.02 mole) was suspended in 20% (v/v) aqueous acetic acid and concentrated H$_2$SO$_4$ (0.279 ml). The mixture was stirred and heated at 60° C. Iodine (2 g, 0.008 mole) and periodic acid (2.76 g, 0.012 mole) was added to the mixture. The reaction mixture was stirred for one hr at the same temperature, cooled, poured into water and extracted with chloroform. The chloroform extract was washed with aqueous sodium bisulphite solution, washed with water and dried (Na$_2$SO$_4$). The chloroform extract was poured onto a column of 250 g of silica gel (prepared with 10% (v/v) ethyl acetate in hexane). The column was eluted with 1.5 liters of the same solvent system and then with 20% (v/v) ethyl acetate in hexane. The appropriate fractions were combined to give 5-iodo-4,6-dimethoxy-1-naphthalenecarboxylic acid methyl ester (1.4 g, 80% pure). The pure compound, mp 120°–122° C., was obtained by crystallization from ethyl acetate-hexane.

A mixture of the latter compound (7.1 g, 0.019 mole), freshly prepared copper powder (4.5 g, prepared according to the procedure of R. Q. Brewster and T. Groening, "Organic Synthesis", Coll. Vol. II, John Wiley and Sons, New York, N.Y., U.S.A., 1948, p. 445), trifluoromethyl iodide (8.5 g, 0.43 mole) and dry pyridine (35 ml) was heated for 20 hr at 120° C. in an autoclave. After cooling to 22° to 24° C., the mixture was taken up in toluene and the toluene suspension was filtered. The filtrate was concentrated to dryness under reduced pressure. The residue was dissolved in chloroform. Insoluble material in the chloroform solution was removed by filtration. The filtrate was passed through a column of 75 g of silica gel and the column was eluted with chloroform. The pure fractions were combined and crystallized from ethyl acetate hexane to give 2.83 g of 4,6-dimethoxy-5-(trifluoromethyl)-1-naphthalenecarboxylic acid methyl ester; mp 120°–123° C., NMR (CDCl$_3$) δ 3.95 (m, 9H), 6.8 and 8.05 (2d, J=10 Hz, 2H), 7.21 and 9.1 (2d, J=10 Hz, 2H).

A suspension of the latter compound (2.83 g, 0.009 mol) in methanol (16.2 ml) and NaOH (5.4 ml of a 4N aqueous solution) was heated at reflux under nitrogen for 10 min. The resulting clear solution was cooled in an ice bath and rendered acid (pH=3) with 2N aqueous HCl. The precipitate was collected, washed with water and dried over P$_2$O$_5$ to give 2.7 g of the title compound, m/e 300 (M+).

EXAMPLE 63

By following serially the procedures of examples 2 and 3 and using an equivalent amount of 4,6-dimethoxy-1-naphthalenecarboxylic acid of example 61 instead of 5-bromo-1-naphthalenecarboxylic acid; N-[(4,6-dimethoxy-1-naphthalenyl)thioxomethyl]-N-methylglycine methyl ester (I, R$^1$ and R$^2$=CH$_3$, R$^3$=4—CH$_3$O, R$^4$=6—CH$_3$O and R$^5$=H); mp 105°–107° C.; NMR (CDCl$_3$) δ 3.05 (s, 3H), 3.85 (s, 3H), 3.90 (s, 3H), 4.0 (s, 3H), 4.8 (2d, J=20 Hz, 2H), 7.3 (m, 5H); was obtained via N-[(4,6-dimethoxy-1-naphthalenyl)carbonyl]-N-methylglycine methyl ester; NMR (CDCl$_3$) δ 2.75 (s, 1H), 3.7 (s, 3H), 3.9 (s, 3H), 4.0 (s, 3H), 4.35 (s, 2H), 7.4 (m, 5H).

By following serially the procedures of examples 2 and 3 and using an equivalent amount of 6-methoxy-1-naphthalenecarboxylic acid, described by C. C. Price et al., J. Am. Chem. Soc., 69, 2261 (1947), instead of 5-bromo-1-naphthalenecarboxylic acid, N-[(6-methoxy-1-naphthalenyl)thioxomethyl]-N-methylglycine methyl ester (I, R$^1$ and R$^2$=CH$_3$, R$^3$=6-methoxy, and R$^4$ and R$^5$=H), NMR (CDCl$_3$) δ 3.02 (s, 3H), 3.86 (s, 3H), 3.89 (s, 3H), 4.53 & 4.35 (d, J=17 Hz, 2H), 6.90–8.10 (m, 6H), was obtained via N-[(6-methoxy-1-naphthalenyl)carbonyl]-N-methylglycine methyl ester.

By following serially the procedures of examples 2 and 3 and using an equivalent amount of 4,6-dimethoxy-5-(trifluoromethyl)-1-naphthalenecarboxylic acid of example 62, instead of 5-bromo-1-naphthalenecarboxylic acid; N-[[4,6-dimethoxy-5-(trifluoromethyl)-1-naphthalenyl]thioxomethyl]-N-methylglycine methyl ester (I, R$^1$ and R$^2$=CH$_3$O, R$^3$=4—CH$_3$O, R$^4$=5—CF$_3$ and R$^5$=6—CH$_3$O), NMR (CDCl$_3$) δ 3.0 (s, 3H), 3.7 (s, 3H), 3.85 (s, 3H), 3.95 (s, 3H), 4.35 & 5.45 (2d, J=17 Hz, 2H), 6.8–8.2 (m, 4H), was obtained via N-[[4,6-dimethoxy-5-trifluoromethyl)-1-naphthalenyl]carbonyl]-N-methylglycine methyl ester, NMR (CDCl$_3$) δ 2.78 (s, 3H), 3.6 (s, 3H), 3.85 (s, 3H), 3.9 (s, 3H), 4.35 (m, 2H), 6.7–8.3 (m, 4H).

EXAMPLE 64

By following the procedure of example 32, but replacing N-[(5-bromo-1-naphthalenyl)thioxomethyl]-N-methylglycine methyl ester with an equivalent amount of one of the ester compound of formula I in which R$^2$ is lower alkyl, described in example 63, the corresponding compound of formula I in which R$^2$ is hydrogen was obtained, namely, N-[(4,6-dimethoxy-1-naphthalenyl)-thioxomethyl]-N-methylglycine; NMR (DMSO-d$_6$) δ 3.05 (s, 3H), 3.90 (s, 3H), 3.97 (s, 3H), 4.27 & 4.67 (2d, J=17 Hz, 2H), 6.50–8.00 (m, 5H), 9.12 (broad, 1H); IR CHCl$_3$) 2900, 1720 cm$^{-1}$; UVλmax (MeOH) 337 nm (ε10,280), 322 (9,675), 278 (35,385) shoulder at 242 (66,830), 224 (114,600); Anal Calcd: C, 60.17% H. 5.36% N, 4.38%; Found: C, 58.38% H, 5.20% N, 4.80%; N-[(6-methoxy-1-naphthalenyl)thioxomethyl]-N-methylglycine; mp 153°–154° C., NMR (DMSO-d$_6$) δ2.95 (s, 3H), 3.9 (s, 3H), 4.65 and 5.2 (2d, J=16.5 Hz, 2H), 7.5 (m, 6H); and N-[[4,6-dimethoxy-5-(trifluoromethyl)-1-naphthalenyl]thioxomethyl]-N-methylglycine; NMR (CDCl$_3$) d 3.05 (s, 3H), 3.9 (s, 3H), 3.95 (s, 3H), 4.5 & 5.11 (2d, J=17 Hz, 2H), 6.75 (s, 1H), 7.2 (m, 4H); IR (CHCl$_3$) 3000, 1720, 1270, 1130 cm$^{-1}$; Anal Calcd: C, 52.70% H, 4.16% N, 3.61%; Found: C, 52.83% H, 4.46% N, 3.57%.

We claim:

1. A compound of formula I

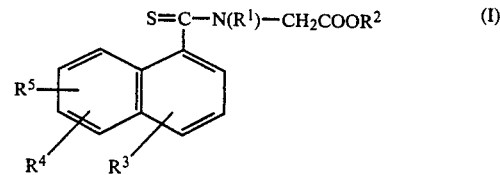

wherein R$^1$ is hydrogen, lower alkyl, lower alkenyl or phenylmethyl; R$^2$ is hydrogen or lower alkyl; R$^3$ is a substituent at position 4, 5 or 8 of the naphthalene ring, the substituent being halo, and R$^4$ and R$^5$ each is hydrogen; or R$^3$ and R$^4$ each is a substituent at different positions selected from positions 3 to 7 of the naphthalene ring, the substituents being selected from the group consisting of lower alkyl, and, halo, (lower)alkoxy(-lower)alkoxy, phenylmethoxy and phenylmethoxy substituted on the phenyl portion with a lower alkyl, lower alkoxy, halo or trihalomethyl, and R$^5$ is hydrogen; or a therapeutically acceptable salt with an organic or inorganic base of the compound of formula I wherein R$^2$ is hydrogen.

2. The compound of claim 1 wherein R$^1$ is hydrogen, lower alkyl, 2-propenyl or phenylmethyl; R$^2$ is hydrogen or lower alkyl; R$^3$ is halo at positions 4, 5 or 8 of the naphthalene ring, and R$^4$ and R$^5$ each is hydrogen; or R$^3$ and R$^4$ are a pair of substituents on the naphthane ring, each substituent being at a different position of the ring, the pair of substituents 5-halo-6-lower alkyl, or a therapeutically acceptable salt with an organic or inorganic base of the compound of formula I wherein R$^2$ is hydrogen.

3. The compound of claim 1 wherein R$^1$ is hydrogen, lower alkyl or phenylmethyl; R$^2$ is hydrogen or lower alkyl; R$^3$ is 4-halo or 5-halo and R$^4$ and R$^5$ each is hydrogen; or R$^3$ and R$^4$ are a pair of substituents on the naphthalene ring selected from the group of pairs consisting of 5-halo-6-lower alkyl, and R$^5$ is hydrogen; or a therapeutically acceptable salt with an organic or inorganic base of the compound of formula I wherein R$^2$ is hydrogen.

4. The compound of claim 1 wherein R$^1$ is lower alkyl; R$^2$ is hydrogen; R$^3$ is 5-halo and R$^4$ and R$^5$ each is hydrogen; or a therapeutically acceptable salt thereof with an organic or inorganic base.

5. N-[(5-Bromo-1-naphthalenyl)thioxomethyl]-N-methylglycine, of the corresponding methyl ester thereof, as claimed in claim 1.

6. N-[(4-Bromo-1-naphthalenyl)thioxomethyl]-N-methylglycine, or the corresponding methyl ester thereof, as claimed in claim 1.

7. N-[(8-Bromo-1-naphthalenyl)thioxomethyl]-N-methylglycine, or the corresponding methyl ester thereof, as claimed in claim 1.

8. N-[(5-Bromo-6-methyl-1-naphthalenyl)thioxomethyl]-N-methylglycine, or the corresponding methyl ester thereof, as claimed in claim 1.

9. N-[(4-Chloro-1-naphthalenyl)thioxomethyl]-N-methylglycine, or the corresponding methyl ester thereof, as claimed in claim 1.

10. N-[(5-Bromo-1-naphthalenyl)thioxomethyl]glycine, or the corresponding methyl ester thereof, as claimed in claim 1.

11. N-[(5-Bromo-1-naphthalenyl)thioxomethyl]-N-propylglycine, or the corresponding methyl ester thereof, as claimed in claim 1.

12. N-[(5-Bromo-1-naphthalenyl)thioxomethyl]-N-(2-propenyl)-glycine, or the corresponding methyl ester thereof, as claimed in claim 1.

13. N-[(5-Bromo-1-naphthalenyl)thioxomethyl]-N-ethylglycine, or the corresponding methyl ester thereof, as claimed in claim 1.

14. N-[(5-Bromo-1-naphthalenyl)thioxomethyl]-N-butylglycine, or the corresponding methyl ester thereof, as claimed in claim 1.

15. N-[(5-Bromo-1-naphthalenyl)thioxomethyl]-N-(phenylmethyl)-glycine, or the corresponding ethyl ester thereof, as claimed in claim 1.

16. A pharmaceutical composition for preventing or relieving diabetic complications in a diabetic mammal, which comprises a compound of claim 1, or a therapeutically acceptable salt thereof with an organic or inorganic base, and a pharmaceutically acceptable carrier.

17. A pharmaceutical composition for preventing or relieving diabetic complications in a diabetic animal which comprises a compound of claim 4, or a therapeutically acceptable salt thereof with an organic or inorganic base, and a pharmaceutically acceptable carrier.

18. A method of preventing or relieving a diabetic complication in a diabetic mammal, which comprises administering to said mammal an alleviating or prophylactic amount of a compound of claim 1, or a therapeutically acceptable salt thereof with an organic or inorganic base.

19. The method of claim 18 wherein the diabetic complications are selected for neuropathy, nephropathy, retinopathy and cataracts.

20. A method of preventing or relieving diabetic complications in a diabetic mammal, which comprises administering to said mammal an alleviating or prophylactic amount of a compound of claim 4, or a therapeutically acceptable salt thereof with an organic or inorganic base.

* * * * *